US010117702B2

(12) United States Patent
Danziger et al.

(10) Patent No.: US 10,117,702 B2
(45) Date of Patent: Nov. 6, 2018

(54) SURGICAL GENERATOR SYSTEMS AND RELATED METHODS

(71) Applicant: Ethicon Endo-Surgery, LLC, Guaynabo, PR (US)

(72) Inventors: Benjamin J. Danziger, Cincinnati, OH (US); Jeffrey L. Aldridge, Lebanon, OH (US); Robert A. Kemerling, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 307 days.

(21) Appl. No.: 14/683,358

(22) Filed: Apr. 10, 2015

(65) Prior Publication Data

US 2016/0296271 A1    Oct. 13, 2016

(51) Int. Cl.
*A61B 18/12* (2006.01)
*A61B 18/00* (2006.01)

(52) U.S. Cl.
CPC ...... *A61B 18/1206* (2013.01); *A61B 18/1233* (2013.01); *A61B 2018/0072* (2013.01);
(Continued)

(58) Field of Classification Search
CPC .......... A61B 18/12106; A61B 18/1233; A61B 2018/00642; A61B 2018/00672;
(Continued)

(56) References Cited

U.S. PATENT DOCUMENTS

| 2,366,274 A | 1/1945 | Luth et al. |
| 2,458,152 A | 1/1949 | Eakins |

(Continued)

FOREIGN PATENT DOCUMENTS

| CN | 2868227 Y | 2/2007 |
| CN | 102834069 A | 12/2012 |

(Continued)

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

(Continued)

*Primary Examiner* — Daniel Fowler
*Assistant Examiner* — Tigist Demie

(57) ABSTRACT

Surgical generator systems and related methods are disclosed herein. An exemplary generator system can include one or more auxiliary transformer stages to boost the amount of power applied to low-impedance tissue, or to adjust the output voltage and current delivered to a surgical instrument. The auxiliary transformer stage(s) can be disposed in the generator, in the surgical instrument, and/or in an intermediate component. Exemplary generator systems can also include an accessory box disposed inline between a generator and a surgical instrument to provide expanded functionality to the system. The accessory box can have a ground plane that is isolated from the ground planes of the mains supply, the generator, and/or the surgical instrument to reduce or eliminate patient leakage current.

12 Claims, 7 Drawing Sheets

(52) U.S. Cl.
CPC .............. *A61B 2018/00642* (2013.01); *A61B 2018/00672* (2013.01); *A61B 2018/00767* (2013.01); *A61B 2018/00875* (2013.01); *A61B 2018/1286* (2013.01)

(58) Field of Classification Search
CPC .. A61B 2018/0072; A61B 2018/00767; A61B 2018/00875; A61B 2018/1286; A61B 18/1206
See application file for complete search history.

(56) References Cited

U.S. PATENT DOCUMENTS

| | | |
|---|---|---|
| 2,510,693 A | 6/1950 | Green |
| 2,867,039 A | 1/1959 | Zach |
| 3,166,971 A | 1/1965 | Stoecker |
| 3,525,912 A | 8/1970 | Wallin |
| 3,580,841 A | 5/1971 | Cadotte et al. |
| 3,703,651 A | 11/1972 | Blowers |
| 3,777,760 A | 12/1973 | Essner |
| 4,005,714 A | 2/1977 | Hiltebrandt |
| 4,034,762 A | 7/1977 | Cosens et al. |
| 4,058,126 A | 11/1977 | Leveen |
| 4,203,430 A | 5/1980 | Takahashi |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,314,559 A | 2/1982 | Allen |
| 4,463,759 A | 8/1984 | Garito et al. |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,617,927 A | 10/1986 | Manes |
| 4,735,603 A | 4/1988 | Goodson et al. |
| 4,761,871 A | 8/1988 | O'Connor et al. |
| 4,830,462 A | 5/1989 | Karny et al. |
| 4,849,133 A | 7/1989 | Yoshida et al. |
| 4,860,745 A | 8/1989 | Farin et al. |
| 4,878,493 A | 11/1989 | Pasternak et al. |
| 4,880,015 A | 11/1989 | Nierman |
| 4,910,389 A | 3/1990 | Sherman et al. |
| 4,920,978 A | 5/1990 | Colvin |
| 4,936,842 A | 6/1990 | D'Amelio et al. |
| 5,020,514 A | 6/1991 | Heckele |
| 5,061,269 A | 10/1991 | Muller |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,156,633 A | 10/1992 | Smith |
| 5,160,334 A | 11/1992 | Billings et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,217,460 A | 6/1993 | Knoepfler |
| 5,234,428 A | 8/1993 | Kaufman |
| 5,258,006 A | 11/1993 | Rydell et al. |
| 5,285,945 A | 2/1994 | Brinkerhoff et al. |
| 5,290,286 A | 3/1994 | Parins |
| 5,309,927 A | 5/1994 | Welch |
| 5,312,023 A | 5/1994 | Green et al. |
| 5,318,563 A | 6/1994 | Malis et al. |
| 5,318,564 A | 6/1994 | Eggers |
| 5,318,589 A | 6/1994 | Lichtman |
| 5,326,013 A | 7/1994 | Green et al. |
| 5,330,471 A | 7/1994 | Eggers |
| 5,330,502 A | 7/1994 | Hassler et al. |
| 5,339,723 A | 8/1994 | Huitema |
| 5,342,359 A | 8/1994 | Rydell |
| 5,361,583 A | 11/1994 | Huitema |
| 5,383,874 A | 1/1995 | Jackson et al. |
| 5,387,207 A | 2/1995 | Dyer et al. |
| 5,389,098 A | 2/1995 | Tsuruta et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,417,709 A | 5/1995 | Slater |
| 5,428,504 A | 6/1995 | Bhatla |
| 5,429,131 A | 7/1995 | Scheinman et al. |
| 5,443,463 A | 8/1995 | Stern et al. |
| 5,445,638 A | 8/1995 | Rydell et al. |
| 5,451,227 A | 9/1995 | Michaelson |
| 5,456,684 A | 10/1995 | Schmidt et al. |
| 5,458,598 A | 10/1995 | Feinberg et al. |
| 5,465,895 A | 11/1995 | Knodel et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,484,436 A | 1/1996 | Eggers et al. |
| 5,486,189 A | 1/1996 | Mudry et al. |
| 5,496,317 A | 3/1996 | Goble et al. |
| 5,504,650 A | 4/1996 | Katsui et al. |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,681 A | 7/1996 | Strul et al. |
| 5,542,916 A | 8/1996 | Hirsch et al. |
| 5,558,671 A | 9/1996 | Yates |
| 5,563,179 A | 10/1996 | Stone et al. |
| 5,569,164 A | 10/1996 | Lurz |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,607,450 A | 3/1997 | Zvenyatsky et al. |
| 5,611,813 A | 3/1997 | Lichtman |
| 5,618,307 A | 4/1997 | Donlon et al. |
| 5,624,452 A | 4/1997 | Yates |
| 5,632,432 A | 5/1997 | Schulze et al. |
| 5,647,871 A | 7/1997 | Levine et al. |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,674,219 A | 10/1997 | Monson et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,711,472 A | 1/1998 | Bryan |
| 5,713,896 A | 2/1998 | Nardella |
| 5,716,366 A | 2/1998 | Yates |
| 5,720,742 A | 2/1998 | Zacharias |
| 5,720,744 A | 2/1998 | Eggleston et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,810,811 A | 9/1998 | Yates et al. |
| 5,817,033 A | 10/1998 | DeSantis et al. |
| 5,817,084 A | 10/1998 | Jensen |
| 5,817,093 A | 10/1998 | Williamson, IV et al. |
| 5,827,323 A | 10/1998 | Klieman |
| 5,836,909 A | 11/1998 | Cosmescu |

(56) References Cited

U.S. PATENT DOCUMENTS

| | | | |
|---|---|---|---|
| 5,836,943 A | 11/1998 | Miller, III | |
| 5,836,990 A | 11/1998 | Li | |
| 5,853,412 A | 12/1998 | Mayenberger | |
| 5,876,401 A | 3/1999 | Schulze et al. | |
| 5,878,193 A | 3/1999 | Wang et al. | |
| 5,880,668 A | 3/1999 | Hall | |
| 5,891,142 A | 4/1999 | Eggers et al. | |
| 5,906,625 A | 5/1999 | Bito et al. | |
| 5,910,129 A | 6/1999 | Koblish et al. | |
| 5,921,956 A | 7/1999 | Grinberg et al. | |
| 5,929,846 A | 7/1999 | Rosenberg et al. | |
| 5,984,938 A | 11/1999 | Yoon | |
| 6,003,517 A | 12/1999 | Sheffield et al. | |
| 6,013,052 A | 1/2000 | Durman et al. | |
| 6,024,741 A | 2/2000 | Williamson, IV et al. | |
| 6,024,744 A | 2/2000 | Kese et al. | |
| 6,033,399 A | 3/2000 | Gines | |
| 6,039,734 A | 3/2000 | Goble | |
| 6,050,996 A | 4/2000 | Schmaltz et al. | |
| 6,063,098 A | 5/2000 | Houser et al. | |
| 6,068,629 A | 5/2000 | Haissaguerre et al. | |
| 6,074,389 A | 6/2000 | Levine et al. | |
| 6,091,995 A | 7/2000 | Ingle et al. | |
| 6,099,483 A | 8/2000 | Palmer et al. | |
| 6,099,550 A | 8/2000 | Yoon | |
| H1904 H | 10/2000 | Yates et al. | |
| 6,132,368 A | 10/2000 | Cooper | |
| 6,144,402 A | 11/2000 | Norsworthy et al. | |
| 6,152,923 A | 11/2000 | Ryan | |
| 6,154,198 A | 11/2000 | Rosenberg | |
| 6,162,208 A | 12/2000 | Hipps | |
| 6,174,309 B1 | 1/2001 | Wrublewski et al. | |
| 6,176,857 B1 | 1/2001 | Ashley | |
| 6,190,386 B1 | 2/2001 | Rydell | |
| 6,206,876 B1 | 3/2001 | Levine et al. | |
| 6,228,080 B1 | 5/2001 | Gines | |
| 6,231,565 B1 | 5/2001 | Tovey et al. | |
| 6,259,230 B1 | 7/2001 | Chou | |
| 6,277,117 B1 | 8/2001 | Tetzlaff et al. | |
| 6,292,700 B1 | 9/2001 | Morrison et al. | |
| 6,325,799 B1 * | 12/2001 | Goble | A61B 18/12 606/34 |
| 6,340,878 B1 | 1/2002 | Oglesbee | |
| 6,364,888 B1 | 4/2002 | Niemeyer et al. | |
| 6,387,109 B1 | 5/2002 | Davison et al. | |
| 6,391,026 B1 | 5/2002 | Hung et al. | |
| 6,398,779 B1 | 6/2002 | Buysse et al. | |
| 6,409,722 B1 | 6/2002 | Hoey et al. | |
| H2037 H | 7/2002 | Yates et al. | |
| 6,419,675 B1 | 7/2002 | Gallo, Sr. | |
| 6,430,446 B1 | 8/2002 | Knowlton | |
| 6,443,968 B1 | 9/2002 | Holthaus et al. | |
| 6,458,128 B1 | 10/2002 | Schulze | |
| 6,464,689 B1 | 10/2002 | Qin et al. | |
| 6,464,702 B2 | 10/2002 | Schulze et al. | |
| 6,480,796 B2 | 11/2002 | Wiener | |
| 6,491,690 B1 | 12/2002 | Goble et al. | |
| 6,500,112 B1 | 12/2002 | Khouri | |
| 6,500,176 B1 | 12/2002 | Truckai et al. | |
| 6,503,248 B1 | 1/2003 | Levine | |
| 6,511,480 B1 | 1/2003 | Tetzlaff et al. | |
| 6,514,252 B2 | 2/2003 | Nezhat et al. | |
| 6,517,565 B1 | 2/2003 | Whitman et al. | |
| 6,531,846 B1 | 3/2003 | Smith | |
| 6,533,784 B2 | 3/2003 | Truckai et al. | |
| 6,537,272 B2 | 3/2003 | Christopherson et al. | |
| 6,537,291 B2 | 3/2003 | Friedman et al. | |
| 6,551,309 B1 | 4/2003 | LePivert | |
| 6,554,829 B2 | 4/2003 | Schulze et al. | |
| 6,558,376 B2 | 5/2003 | Bishop | |
| 6,562,037 B2 | 5/2003 | Paton et al. | |
| 6,572,639 B1 | 6/2003 | Ingle et al. | |
| 6,575,969 B1 | 6/2003 | Rittman, III et al. | |
| 6,582,451 B1 | 6/2003 | Marucci et al. | |
| 6,584,360 B2 | 6/2003 | Francischelli et al. | |
| 6,585,735 B1 | 7/2003 | Frazier et al. | |
| 6,589,200 B1 | 7/2003 | Schwemberger et al. | |
| 6,602,252 B2 | 8/2003 | Mollenauer | |
| 6,610,060 B2 | 8/2003 | Mulier et al. | |
| 6,619,529 B2 | 9/2003 | Green et al. | |
| 6,620,161 B2 | 9/2003 | Schulze et al. | |
| 6,622,731 B2 | 9/2003 | Daniel et al. | |
| 6,623,482 B2 | 9/2003 | Pendekanti et al. | |
| 6,635,057 B2 | 10/2003 | Harano et al. | |
| 6,644,532 B2 | 11/2003 | Green et al. | |
| 6,651,669 B1 | 11/2003 | Burnside | |
| 6,656,177 B2 | 12/2003 | Truckai et al. | |
| 6,656,198 B2 | 12/2003 | Tsonton et al. | |
| 6,662,127 B2 | 12/2003 | Wiener et al. | |
| 6,673,248 B2 | 1/2004 | Chowdhury | |
| 6,679,882 B1 | 1/2004 | Kornerup | |
| 6,682,501 B1 | 1/2004 | Nelson et al. | |
| 6,695,840 B2 | 2/2004 | Schulze | |
| 6,722,552 B2 | 4/2004 | Fenton, Jr. | |
| 6,733,498 B2 | 5/2004 | Paton et al. | |
| 6,746,443 B1 | 6/2004 | Morley et al. | |
| 6,752,815 B2 | 6/2004 | Beaupre | |
| 6,766,202 B2 | 7/2004 | Underwood et al. | |
| 6,770,072 B1 | 8/2004 | Truckai et al. | |
| 6,773,409 B2 | 8/2004 | Truckai et al. | |
| 6,773,435 B2 | 8/2004 | Schulze et al. | |
| 6,775,575 B2 | 8/2004 | Bommannan et al. | |
| 6,783,524 B2 | 8/2004 | Anderson et al. | |
| 6,789,939 B2 | 9/2004 | Schrödinger et al. | |
| 6,796,981 B2 | 9/2004 | Wham et al. | |
| 6,800,085 B2 | 10/2004 | Selmon et al. | |
| 6,802,843 B2 | 10/2004 | Truckai et al. | |
| 6,811,842 B1 | 11/2004 | Ehrnsperger et al. | |
| 6,821,273 B2 | 11/2004 | Mollenauer | |
| 6,835,199 B2 | 12/2004 | McGuckin, Jr. et al. | |
| 6,840,938 B1 | 1/2005 | Morley et al. | |
| 6,860,880 B2 | 3/2005 | Treat et al. | |
| 6,877,647 B2 | 4/2005 | Green et al. | |
| 6,893,435 B2 | 5/2005 | Goble | |
| 6,905,497 B2 | 6/2005 | Truckai et al. | |
| 6,908,463 B2 | 6/2005 | Treat et al. | |
| 6,913,579 B2 | 7/2005 | Truckai et al. | |
| 6,926,716 B2 | 8/2005 | Baker et al. | |
| 6,929,622 B2 | 8/2005 | Chian | |
| 6,929,644 B2 | 8/2005 | Truckai et al. | |
| 6,953,461 B2 | 10/2005 | McClurken et al. | |
| 6,977,495 B2 | 12/2005 | Donofrio | |
| 6,994,709 B2 | 2/2006 | Iida | |
| 7,000,818 B2 | 2/2006 | Shelton, IV et al. | |
| 7,011,657 B2 | 3/2006 | Truckai et al. | |
| 7,041,102 B2 | 5/2006 | Truckai et al. | |
| 7,052,496 B2 | 5/2006 | Yamauchi | |
| 7,055,731 B2 | 6/2006 | Shelton, IV et al. | |
| 7,063,699 B2 | 6/2006 | Hess et al. | |
| 7,066,936 B2 | 6/2006 | Ryan | |
| 7,070,597 B2 | 7/2006 | Truckai et al. | |
| 7,077,853 B2 | 7/2006 | Kramer et al. | |
| 7,083,618 B2 | 8/2006 | Couture et al. | |
| 7,083,619 B2 | 8/2006 | Truckai et al. | |
| 7,087,054 B2 | 8/2006 | Truckai et al. | |
| 7,094,235 B2 | 8/2006 | Francischelli et al. | |
| 7,101,371 B2 | 9/2006 | Dycus et al. | |
| 7,101,372 B2 | 9/2006 | Dycus et al. | |
| 7,101,373 B2 | 9/2006 | Dycus et al. | |
| 7,112,201 B2 | 9/2006 | Truckai et al. | |
| 7,118,570 B2 | 10/2006 | Tetzlaff et al. | |
| 7,125,409 B2 | 10/2006 | Truckai et al. | |
| 7,131,970 B2 | 11/2006 | Moses et al. | |
| 7,137,980 B2 | 11/2006 | Buysse et al. | |
| 7,143,925 B2 | 12/2006 | Shelton, IV et al. | |
| 7,147,138 B2 | 12/2006 | Shelton, IV | |
| 7,156,846 B2 | 1/2007 | Dycus et al. | |
| 7,160,296 B2 | 1/2007 | Pearson et al. | |
| 7,169,146 B2 | 1/2007 | Truckai et al. | |
| 7,169,156 B2 | 1/2007 | Hart | |
| 7,179,271 B2 | 2/2007 | Friedman et al. | |
| 7,186,253 B2 | 3/2007 | Truckai et al. | |
| 7,189,233 B2 | 3/2007 | Truckai et al. | |
| 7,195,631 B2 | 3/2007 | Dumbauld | |

(56) References Cited

U.S. PATENT DOCUMENTS

| | | | |
|---|---|---|---|
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,226,448 B2 | 6/2007 | Bertolero et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |
| 7,252,667 B2 | 8/2007 | Moses et al. |
| 7,267,677 B2 | 9/2007 | Johnson et al. |
| 7,267,685 B2 | 9/2007 | Butaric et al. |
| 7,273,483 B2 | 9/2007 | Wiener et al. |
| 7,287,682 B1 | 10/2007 | Ezzat et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,384,420 B2 | 6/2008 | Dycus et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,416,101 B2 | 8/2008 | Shelton, IV et al. |
| 7,422,139 B2 | 9/2008 | Shelton, IV et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,494,501 B2 | 2/2009 | Ahlberg et al. |
| 7,498,080 B2 | 3/2009 | Tung et al. |
| 7,506,791 B2 | 3/2009 | Omaits et al. |
| 7,510,107 B2 | 3/2009 | Timm et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,540,872 B2 | 6/2009 | Schechter et al. |
| 7,543,730 B1 | 6/2009 | Marczyk |
| 7,550,216 B2 | 6/2009 | Ofer et al. |
| 7,553,309 B2 | 6/2009 | Buysse et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,621,930 B2 | 11/2009 | Houser |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,691,095 B2 | 4/2010 | Bednarek et al. |
| 7,691,098 B2 | 4/2010 | Wallace et al. |
| 7,703,459 B2 | 4/2010 | Saadat et al. |
| 7,703,653 B2 | 4/2010 | Shah et al. |
| 7,708,751 B2 | 5/2010 | Hughes et al. |
| 7,717,915 B2 | 5/2010 | Miyazawa |
| 7,722,527 B2 | 5/2010 | Bouchier et al. |
| 7,722,607 B2 | 5/2010 | Dumbauld et al. |
| 7,726,537 B2 | 6/2010 | Olson et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,210 B2 | 8/2010 | Shelton, IV et al. |
| 7,766,910 B2 | 8/2010 | Hixson et al. |
| 7,770,775 B2 | 8/2010 | Shelton, IV et al. |
| 7,775,972 B2 | 8/2010 | Brock et al. |
| 7,776,037 B2 | 8/2010 | Odom |
| 7,780,651 B2 | 8/2010 | Madhani et al. |
| 7,780,663 B2 | 8/2010 | Yates et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,803,156 B2 | 9/2010 | Eder et al. |
| 7,806,891 B2 | 10/2010 | Nowlin et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Sheltoin, IV et al. |
| 7,819,872 B2 | 10/2010 | Johnson et al. |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |
| 7,861,906 B2 | 1/2011 | Doll et al. |
| 7,879,035 B2 | 2/2011 | Garrison et al. |
| 7,879,070 B2 | 2/2011 | Ortiz et al. |
| 7,896,875 B2 | 3/2011 | Heim et al. |
| 7,901,400 B2 | 3/2011 | Wham et al. |
| 7,909,220 B2 | 3/2011 | Viola |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,649 B2 | 4/2011 | Couture et al. |
| 7,935,114 B2 | 5/2011 | Takashino et al. |
| 7,951,165 B2 | 5/2011 | Golden et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 7,997,278 B2 | 8/2011 | Utley et al. |
| 8,020,743 B2 | 9/2011 | Shelton, IV |
| 8,038,693 B2 | 10/2011 | Allen |
| 8,056,720 B2 | 11/2011 | Hawkes |
| 8,058,771 B2 | 11/2011 | Giordano et al. |
| 8,061,014 B2 | 11/2011 | Smith et al. |
| 8,070,036 B1 | 12/2011 | Knodel et al. |
| 8,105,323 B2 | 1/2012 | Buysse et al. |
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,221,415 B2 | 7/2012 | Francischelli |
| 8,236,020 B2 | 8/2012 | Smith et al. |
| 8,241,235 B2 | 8/2012 | Kahler et al. |
| 8,241,284 B2 | 8/2012 | Dycus et al. |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,267,300 B2 | 9/2012 | Boudreaux |
| 8,277,446 B2 | 10/2012 | Heard |
| 8,277,447 B2 | 10/2012 | Garrison et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,298,232 B2 | 10/2012 | Unger |

(56) References Cited

U.S. PATENT DOCUMENTS

| | | |
|---|---|---|
| 8,303,583 B2 | 11/2012 | Hosier et al. |
| 8,323,310 B2 | 12/2012 | Kingsley |
| 8,333,778 B2 | 12/2012 | Smith et al. |
| 8,333,779 B2 | 12/2012 | Smith et al. |
| 8,334,468 B2 | 12/2012 | Palmer et al. |
| 8,338,726 B2 | 12/2012 | Palmer et al. |
| 8,357,158 B2 | 1/2013 | McKenna et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,377,059 B2 | 2/2013 | Deville et al. |
| 8,377,085 B2 | 2/2013 | Smith et al. |
| 8,397,971 B2 | 3/2013 | Yates et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,425,545 B2 | 4/2013 | Smith et al. |
| 8,430,876 B2 | 4/2013 | Kappus et al. |
| 8,435,257 B2 | 5/2013 | Smith et al. |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,480,703 B2 | 7/2013 | Nicholas et al. |
| 8,485,413 B2 | 7/2013 | Scheib et al. |
| 8,486,057 B2 | 7/2013 | Behnke, II |
| 8,496,682 B2 | 7/2013 | Guerra et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,591,506 B2 | 11/2013 | Wham et al. |
| D695,407 S | 12/2013 | Price et al. |
| 8,613,383 B2 | 12/2013 | Beckman et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,638,428 B2 | 1/2014 | Brown |
| 8,647,350 B2 | 2/2014 | Mohan et al. |
| 8,663,220 B2 | 3/2014 | Wiener et al. |
| 8,663,222 B2 | 3/2014 | Anderson et al. |
| 8,684,253 B2 | 4/2014 | Giordano et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,764,747 B2 | 7/2014 | Cummings et al. |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,827,992 B2 | 9/2014 | Koss et al. |
| 8,834,466 B2 | 9/2014 | Cummings et al. |
| 8,834,518 B2 | 9/2014 | Faller et al. |
| 8,845,630 B2 | 9/2014 | Mehta et al. |
| 8,888,776 B2 | 11/2014 | Dietz et al. |
| 8,888,809 B2 | 11/2014 | Davison et al. |
| 8,906,016 B2 | 12/2014 | Boudreaux et al. |
| 8,926,607 B2 | 1/2015 | Norvell et al. |
| 8,926,608 B2 | 1/2015 | Bacher et al. |
| 8,931,682 B2 | 1/2015 | Timm et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,979,843 B2 | 3/2015 | Timm et al. |
| 8,979,844 B2 | 3/2015 | White et al. |
| 8,979,890 B2 | 3/2015 | Boudreaux |
| 8,992,422 B2 | 3/2015 | Spivey et al. |
| 9,005,199 B2 | 4/2015 | Beckman et al. |
| 9,011,437 B2 | 4/2015 | Woodruff et al. |
| 9,028,494 B2 | 5/2015 | Shelton, IV et al. |
| 9,028,519 B2 | 5/2015 | Yates et al. |
| 9,044,243 B2 | 6/2015 | Johnson et al. |
| 9,044,256 B2 | 6/2015 | Cadeddu et al. |
| 9,055,961 B2 | 6/2015 | Manzo et al. |
| 9,060,770 B2 | 6/2015 | Shelton, IV et al. |
| 9,066,723 B2 | 6/2015 | Beller et al. |
| 9,072,535 B2 | 7/2015 | Shelton, IV et al. |
| 9,072,536 B2 | 7/2015 | Shelton, IV et al. |
| 9,101,385 B2 | 8/2015 | Shelton, IV et al. |
| 9,119,657 B2 | 9/2015 | Shelton, IV et al. |
| 9,125,662 B2 | 9/2015 | Shelton, IV |
| 9,149,324 B2 | 10/2015 | Huang et al. |
| 9,149,325 B2 | 10/2015 | Worrell et al. |
| 9,168,085 B2 | 10/2015 | Juzkiw et al. |
| 9,179,912 B2 | 11/2015 | Yates et al. |
| 9,192,380 B2 | 11/2015 | (Tarinelli) Racenet et al. |
| 9,192,431 B2 | 11/2015 | Woodruff et al. |
| 9,198,714 B2 | 12/2015 | Worrell et al. |
| 9,204,879 B2 | 12/2015 | Shelton, IV |
| 9,216,050 B2 | 12/2015 | Condie et al. |
| 9,226,751 B2 | 1/2016 | Shelton, IV et al. |
| 9,226,767 B2 | 1/2016 | Stulen et al. |
| 9,237,891 B2 | 1/2016 | Shelton, IV |
| 9,259,265 B2 | 2/2016 | Harris et al. |
| 9,265,926 B2 | 2/2016 | Strobl et al. |
| 9,277,962 B2 | 3/2016 | Koss et al. |
| 9,283,027 B2 | 3/2016 | Monson et al. |
| 9,283,045 B2 | 3/2016 | Rhee et al. |
| 9,295,514 B2 | 3/2016 | Shelton, IV et al. |
| 9,314,292 B2 | 4/2016 | Trees et al. |
| 9,326,788 B2 | 5/2016 | Batross et al. |
| 9,333,025 B2 | 5/2016 | Monson et al. |
| 9,351,754 B2 | 5/2016 | Vakharia et al. |
| 9,375,232 B2 | 6/2016 | Hunt et al. |
| 9,375,267 B2 | 6/2016 | Kerr et al. |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,863 B2 | 10/2016 | Moua |
| 9,456,864 B2 | 10/2016 | Witt et al. |
| 9,510,906 B2 | 12/2016 | Boudreaux et al. |
| 9,522,029 B2 | 12/2016 | Yates et al. |
| 2002/0022836 A1 | 2/2002 | Goble et al. |
| 2002/0049551 A1 | 4/2002 | Friedman et al. |
| 2002/0107517 A1 | 8/2002 | Witt et al. |
| 2002/0165541 A1 | 11/2002 | Whitman |
| 2003/0014053 A1 | 1/2003 | Nguyen et al. |
| 2003/0105474 A1 | 6/2003 | Bonutti |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0216722 A1 | 11/2003 | Swanson |
| 2003/0229344 A1 | 12/2003 | Dycus et al. |
| 2004/0019350 A1 | 1/2004 | O'Brien et al. |
| 2004/0054364 A1 | 3/2004 | Aranyi et al. |
| 2004/0092992 A1 | 5/2004 | Adams et al. |

(56) References Cited

U.S. PATENT DOCUMENTS

| | | |
|---|---|---|
| 2004/0138621 A1 | 7/2004 | Jahns et al. |
| 2004/0167508 A1 | 8/2004 | Wham et al. |
| 2004/0193148 A1 | 9/2004 | Wham et al. |
| 2004/0193150 A1 | 9/2004 | Sharkey et al. |
| 2004/0232196 A1 | 11/2004 | Shelton, IV et al. |
| 2004/0249374 A1 | 12/2004 | Tetzlaff et al. |
| 2004/0260273 A1 | 12/2004 | Wan |
| 2005/0015125 A1 | 1/2005 | Mioduski et al. |
| 2005/0033278 A1 | 2/2005 | McClurken et al. |
| 2005/0085809 A1 | 4/2005 | Mucko et al. |
| 2005/0090817 A1 | 4/2005 | Phan |
| 2005/0103819 A1 | 5/2005 | Racenet et al. |
| 2005/0131390 A1 | 6/2005 | Heinrich et al. |
| 2005/0165429 A1 | 7/2005 | Douglas et al. |
| 2005/0171522 A1 | 8/2005 | Christopherson |
| 2005/0203507 A1 | 9/2005 | Truckai et al. |
| 2005/0256405 A1 | 11/2005 | Makin et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0058825 A1 | 3/2006 | Ogura et al. |
| 2006/0064086 A1 | 3/2006 | Odom |
| 2006/0069388 A1 | 3/2006 | Truckai et al. |
| 2006/0116675 A1* | 6/2006 | McClurken ............ A61B 18/14 606/51 |
| 2006/0159731 A1 | 7/2006 | Shoshan |
| 2006/0270916 A1 | 11/2006 | Skwarek et al. |
| 2006/0293656 A1 | 12/2006 | Shadduck et al. |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0106317 A1 | 5/2007 | Shelton, IV et al. |
| 2007/0118115 A1 | 5/2007 | Artale et al. |
| 2007/0146113 A1 | 6/2007 | Truckai et al. |
| 2007/0173803 A1 | 7/2007 | Wham et al. |
| 2007/0173811 A1 | 7/2007 | Couture et al. |
| 2007/0173813 A1 | 7/2007 | Odom |
| 2007/0175949 A1 | 8/2007 | Shelton, IV et al. |
| 2007/0185474 A1 | 8/2007 | Nahen |
| 2007/0191713 A1 | 8/2007 | Eichmann et al. |
| 2007/0191830 A1 | 8/2007 | Cromton, Jr. et al. |
| 2007/0203483 A1 | 8/2007 | Kim et al. |
| 2007/0208312 A1 | 9/2007 | Norton et al. |
| 2007/0208340 A1 | 9/2007 | Ganz et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |
| 2007/0260242 A1 | 11/2007 | Dycus et al. |
| 2007/0265613 A1 | 11/2007 | Edelstein et al. |
| 2007/0265616 A1 | 11/2007 | Couture et al. |
| 2008/0015575 A1 | 1/2008 | Odom et al. |
| 2008/0071269 A1 | 3/2008 | Hilario et al. |
| 2008/0108985 A1* | 5/2008 | Konesky ............... A61B 18/042 606/27 |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0167522 A1 | 7/2008 | Giordano et al. |
| 2008/0188755 A1 | 8/2008 | Hart |
| 2008/0188851 A1 | 8/2008 | Truckai et al. |
| 2008/0188912 A1 | 8/2008 | Stone et al. |
| 2008/0214967 A1 | 9/2008 | Aranyi et al. |
| 2008/0221565 A1 | 9/2008 | Eder et al. |
| 2008/0255642 A1 | 10/2008 | Zarins et al. |
| 2008/0262491 A1 | 10/2008 | Swoyer et al. |
| 2008/0269862 A1 | 10/2008 | Elmouelhi et al. |
| 2008/0281315 A1 | 11/2008 | Gines |
| 2008/0294158 A1 | 11/2008 | Pappone et al. |
| 2008/0300588 A1 | 12/2008 | Groth et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0082766 A1 | 3/2009 | Unger et al. |
| 2009/0099582 A1 | 4/2009 | Isaacs et al. |
| 2009/0112229 A1 | 4/2009 | Omori et al. |
| 2009/0125026 A1 | 5/2009 | Rioux et al. |
| 2009/0125027 A1 | 5/2009 | Fischer |
| 2009/0131929 A1 | 5/2009 | Shimizu |
| 2009/0138003 A1 | 5/2009 | Deville et al. |
| 2009/0138006 A1 | 5/2009 | Bales et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0248021 A1 | 10/2009 | McKenna |
| 2009/0254080 A1 | 10/2009 | Honda |
| 2009/0287205 A1 | 11/2009 | Ingle |
| 2009/0320268 A1 | 12/2009 | Cunningham et al. |
| 2009/0326530 A1 | 12/2009 | Orban, III et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0168620 A1 | 7/2010 | Klimovitch et al. |
| 2010/0222752 A1 | 9/2010 | Collins, Jr. et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0015627 A1 | 1/2011 | DiNardo et al. |
| 2011/0082486 A1 | 4/2011 | Messerly et al. |
| 2011/0087212 A1 | 4/2011 | Aldridge et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087220 A1 | 4/2011 | Felder et al. |
| 2011/0118754 A1 | 5/2011 | Dachs, II et al. |
| 2011/0155781 A1 | 6/2011 | Swensgard et al. |
| 2011/0224668 A1 | 9/2011 | Johnson et al. |
| 2011/0276049 A1 | 11/2011 | Gerhardt |
| 2011/0276057 A1 | 11/2011 | Conlon et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295269 A1 | 12/2011 | Swensgard et al. |
| 2011/0295295 A1 | 12/2011 | Shelton, IV et al. |
| 2011/0301605 A1 | 12/2011 | Horner |
| 2011/0306967 A1 | 12/2011 | Payne et al. |
| 2011/0313415 A1 | 12/2011 | Fernandez et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0041435 A1* | 2/2012 | Schall ............... A61B 18/1206 606/34 |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |
| 2012/0109186 A1 | 5/2012 | Parrott et al. |
| 2012/0116265 A1 | 5/2012 | Houser et al. |
| 2012/0116379 A1 | 5/2012 | Yates et al. |
| 2012/0116380 A1 | 5/2012 | Madan et al. |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0138660 A1 | 6/2012 | Shelton, IV |
| 2012/0150170 A1 | 6/2012 | Buysse et al. |

(56) References Cited

U.S. PATENT DOCUMENTS

| | | |
|---|---|---|
| 2012/0150192 A1 | 6/2012 | Dachs, II et al. |
| 2012/0172859 A1 | 7/2012 | Condie et al. |
| 2012/0265196 A1* | 10/2012 | Turner ............ A61B 17/32009 606/34 |
| 2012/0265241 A1 | 10/2012 | Hart et al. |
| 2012/0296371 A1 | 11/2012 | Kappus et al. |
| 2012/0323238 A1 | 12/2012 | Tyrrell et al. |
| 2013/0023925 A1 | 1/2013 | Mueller |
| 2013/0030428 A1 | 1/2013 | Worrell et al. |
| 2013/0030433 A1 | 1/2013 | Heard |
| 2013/0035685 A1 | 2/2013 | Fischer et al. |
| 2013/0079762 A1 | 3/2013 | Twomey et al. |
| 2013/0085496 A1 | 4/2013 | Unger et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0237982 A1* | 9/2013 | Rencher ............ A61B 18/1402 606/39 |
| 2013/0253256 A1 | 9/2013 | Griffith et al. |
| 2013/0253502 A1 | 9/2013 | Aronow et al. |
| 2013/0296843 A1 | 11/2013 | Boudreaux et al. |
| 2013/0338661 A1 | 12/2013 | Behnke, II |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005678 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005701 A1 | 1/2014 | Olson et al. |
| 2014/0005702 A1 | 1/2014 | Timm et al. |
| 2014/0005703 A1 | 1/2014 | Stulen et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0094801 A1 | 4/2014 | Boudreaux et al. |
| 2014/0194875 A1 | 4/2014 | Reschke et al. |
| 2014/0180281 A1 | 6/2014 | Rusin |
| 2014/0194874 A1 | 7/2014 | Dietz et al. |
| 2014/0194915 A1 | 7/2014 | Johnson et al. |
| 2014/0214019 A1 | 7/2014 | Baxter, III et al. |
| 2014/0228844 A1 | 8/2014 | Hörlle et al. |
| 2014/0257284 A1 | 9/2014 | Artale |
| 2014/0276797 A1* | 9/2014 | Batchelor ........... A61B 18/1233 606/42 |
| 2014/0303551 A1 | 10/2014 | Germain et al. |
| 2014/0316408 A1 | 10/2014 | Davison et al. |
| 2014/0330271 A1 | 11/2014 | Dietz et al. |
| 2014/0343550 A1 | 11/2014 | Faller et al. |
| 2015/0018826 A1 | 1/2015 | Boudreaux |
| 2015/0080876 A1 | 3/2015 | Worrell et al. |
| 2015/0080879 A1 | 3/2015 | Trees et al. |
| 2015/0080891 A1 | 3/2015 | Shelton, IV et al. |
| 2015/0133915 A1 | 5/2015 | Strobl et al. |
| 2015/0133929 A1 | 5/2015 | Evans et al. |
| 2015/0141981 A1 | 5/2015 | Price et al. |
| 2015/0190189 A1 | 7/2015 | Yates et al. |
| 2015/0196352 A1 | 7/2015 | Beckman et al. |
| 2015/0230853 A1 | 8/2015 | Johnson et al. |
| 2015/0230861 A1 | 8/2015 | Woloszko et al. |
| 2015/0265347 A1 | 9/2015 | Yates et al. |
| 2015/0272602 A1 | 10/2015 | Boudreaux et al. |
| 2015/0272657 A1 | 10/2015 | Yates et al. |
| 2015/0272659 A1 | 10/2015 | Boudreaux et al. |
| 2015/0272660 A1 | 10/2015 | Boudreaux et al. |
| 2015/0289925 A1 | 10/2015 | Voegele et al. |
| 2015/0297286 A1 | 10/2015 | Boudreaux et al. |
| 2016/0045248 A1 | 2/2016 | Unger et al. |
| 2016/0051315 A1 | 2/2016 | Boudreaux |
| 2016/0051316 A1 | 2/2016 | Boudreaux |
| 2016/0051317 A1 | 2/2016 | Boudreaux |
| 2016/0058492 A1 | 3/2016 | Yates et al. |
| 2016/0074108 A1 | 3/2016 | Woodruff et al. |
| 2016/0128762 A1 | 5/2016 | Harris et al. |
| 2016/0135875 A1 | 5/2016 | Strobl et al. |
| 2016/0157927 A1 | 6/2016 | Corbett et al. |
| 2016/0175024 A1 | 6/2016 | Yates et al. |
| 2016/0175028 A1 | 6/2016 | Trees et al. |
| 2016/0175029 A1 | 6/2016 | Witt et al. |
| 2016/0175030 A1 | 6/2016 | Boudreaux |
| 2016/0175031 A1 | 6/2016 | Boudreaux |
| 2016/0175032 A1 | 6/2016 | Yang |
| 2016/0199123 A1 | 7/2016 | Thomas et al. |
| 2016/0199125 A1 | 7/2016 | Jones |
| 2016/0228171 A1 | 8/2016 | Boudreaux |
| 2016/0270840 A1 | 9/2016 | Yates et al. |
| 2016/0270841 A1 | 9/2016 | Strobl et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296268 A1 | 10/2016 | Gee et al. |
| 2016/0296270 A1 | 10/2016 | Strobl et al. |
| 2016/0302844 A1 | 10/2016 | Strobl et al. |
| 2016/0317215 A1 | 11/2016 | Worrell et al. |

FOREIGN PATENT DOCUMENTS

| | | |
|---|---|---|
| DE | 4300307 A1 | 7/1994 |
| DE | 19608716 C1 | 4/1997 |
| DE | 29623113 U1 | 10/1997 |
| DE | 20004812 U1 | 9/2000 |
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0557806 B1 | 5/1998 |
| EP | 0640317 B1 | 9/1999 |
| EP | 0722696 B1 | 12/2002 |
| EP | 1293172 B1 | 4/2006 |
| EP | 0875209 B1 | 5/2006 |
| EP | 1704824 A1 | 9/2006 |
| EP | 1749479 A1 | 2/2007 |
| EP | 1767157 A1 | 3/2007 |
| EP | 1254637 B1 | 8/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1435852 B1 | 12/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1510178 B1 | 6/2011 |
| EP | 1728475 B1 | 8/2011 |
| EP | 2353518 A1 | 8/2011 |
| EP | 2529681 A1 | 12/2012 |
| EP | 1767164 B1 | 1/2013 |
| EP | 2316359 B1 | 3/2013 |
| EP | 2578172 A2 | 4/2013 |
| EP | 2508143 B1 | 2/2014 |
| GB | 2472216 A | 2/2011 |
| JP | H08-229050 A | 9/1996 |
| JP | 2008-018226 A | 1/2008 |
| JP | 5714508 B2 | 5/2015 |
| WO | WO 81/03272 A1 | 11/1981 |
| WO | WO 93/07817 A1 | 4/1993 |
| WO | WO 93/22973 A1 | 11/1993 |
| WO | WO 95/10978 A1 | 4/1995 |

(56) References Cited

FOREIGN PATENT DOCUMENTS

| | | |
|---|---|---|
| WO | WO 96/35382 A1 | 11/1996 |
| WO | WO 97/10764 A1 | 3/1997 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40857 A1 | 8/1999 |
| WO | WO 99/40861 A1 | 8/1999 |
| WO | WO 00/24330 A1 | 5/2000 |
| WO | WO 00/24331 A1 | 5/2000 |
| WO | WO 00/25691 A1 | 5/2000 |
| WO | WO 01/28444 A1 | 4/2001 |
| WO | WO 02/062241 A1 | 8/2002 |
| WO | WO 02/080797 A1 | 10/2002 |
| WO | WO 03/001986 A2 | 1/2003 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2004/032754 A2 | 4/2004 |
| WO | WO 2004/032762 A1 | 4/2004 |
| WO | WO 2004/032763 A2 | 4/2004 |
| WO | WO 2004/078051 A2 | 9/2004 |
| WO | WO 2004/112618 A2 | 12/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2006/119139 A2 | 11/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/008672 A2 | 1/2011 |
| WO | WO 2011/084768 A1 | 7/2011 |
| WO | WO 2011/089717 A1 | 7/2011 |
| WO | WO 2011/144911 A1 | 11/2011 |
| WO | WO 2012/044606 A2 | 4/2012 |
| WO | WO 2012/166510 A1 | 12/2012 |
| WO | WO 2013/034629 A1 | 3/2013 |
| WO | WO 2013/062978 A2 | 5/2013 |
| WO | WO 2013/102602 A2 | 7/2013 |
| WO | WO 2013/154157 A1 | 10/2013 |
| WO | WO 2015/197395 A8 | 12/2015 |

OTHER PUBLICATIONS

Hörmann et al., "Reversible and irreversible denaturation of collagen fibers." Biochemistry, 10, pp. 932-937 (1971).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-induced changes in the mechanics of a collagenous tissue: pseudoelastic behavior at 37° C," Journal of Biomechanics, 31, pp. 211-216 (1998).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=Ml&sp=1 . . ., accessed Aug. 25, 2009.
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
Kurt Gieck & Reiner Gieck, Engineering Formulas § Z.7 (7th ed. 1997).
National Semiconductors Temperature Sensor Handbook—http://www.national.com/appinfo/tempsensors/files/temphb.pdf; accessed online: Apr. 1, 2011.
Glaser and Subak-Sharpe, Integrated Circuit Engineering, Addison-Wesley Publishing, Reading, MA (1979).
Wright, et al., "Time-Temperature Equivalence of Heat-Induced Changes in Cells and Proteins," Feb., 1998. ASME Journal of Biomechanical Engineering, vol. 120, pp. 22-26.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Covidien Brochure, The LigaSure Precise™ Instrument, dated Mar. 2011 (2 pages).
Erbe Electrosurgery VIO® 200 S, (2012), p. 7, 12 pages, accessed Mar. 31, 2014 at http://www.erbe-med.com/erbe/media/Marketingmaterialien/85140-170_ERBE_EN_VIO_200_S__D027541.
Jang, J. et al. "Neuro-fuzzy and Soft Computing." Prentice Hall, 1997, pp. 13-89, 199-293, 335-393,453-496, 535-549.
Douglas, S.C. "Introduction to Adaptive Filter". Digital Signal Processing Handbook. Ed. Vijay K. Madisetti and Douglas B. Williams. Boca Raton: CRC Press LLC, 1999.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.

(56) References Cited

OTHER PUBLICATIONS

Leonard I. Malis, M.D., "The Value of Irrigation During Bipolar Coagulation," 1989.
U.S. Appl. No. 12/576,529, filed Oct. 9, 2009.
U.S. Appl. No. 15/265,293, filed Sep. 14, 2016.
U.S. Appl. No. 15/258,570, filed Sep. 7, 2016.
U.S. Appl. No. 15/258,578, filed Sep. 7, 2016.
U.S. Appl. No. 15/258,586, filed Sep. 7, 2016.
U.S. Appl. No. 15/258,598, filed Sep. 7, 2016.

* cited by examiner

SURGICAL GENERATOR SYSTEMS AND RELATED METHODS

FIELD

Surgical generator systems and related methods are disclosed herein.

BACKGROUND

Ultrasonic surgical instruments, such as ultrasonic scalpels, are finding increasingly widespread application in surgical procedures by virtue of their unique performance characteristics. Depending upon specific device configurations and operational parameters, ultrasonic surgical instruments can provide substantially simultaneous transection of tissue and haemostasis by coagulation, desirably minimizing patient trauma. An ultrasonic surgical instrument can include an ultrasonic transducer and a distally-mounted end effector (e.g., a blade tip) coupled to the transducer and configured to cut and seal tissue. The end effector transmits ultrasonic energy to tissue brought into contact with the end effector to realize cutting and sealing action. Ultrasonic energy can be transmitted to the end effector by a generator system in communication with the instrument.

Electrosurgical instruments for applying electrical energy to tissue (e.g., in order to treat and/or destroy the tissue) are also finding increasingly widespread application in surgical procedures. An electrosurgical instrument can include a distally-mounted end effector (e.g., having one or more electrodes). The end effector can be positioned against the tissue such that electrical current is introduced into the tissue. Electrosurgical instruments can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flow through the tissue can form haemostatic seals within the tissue and/or between tissues and thus can be particularly useful for sealing blood vessels, for example. The end effector of an electrosurgical instrument can also include a cutting member that is movable relative to the tissue and the electrodes to transect the tissue. Electrical energy can be transmitted to the end effector by a generator system in communication with the instrument. The electrical energy can be in the form of radio frequency ("RF") energy (e.g., in the frequency range of about 100 kHz to about 1 MHz). In operation, an electrosurgical instrument can transmit RF energy through tissue, which can cause ionic agitation, friction, and/or resistive heating, thereby increasing the temperature of the tissue.

Exemplary surgical generator systems for driving ultrasonic surgical devices and/or electrosurgical devices are disclosed in U.S. Pat. No. 8,986,302 issued on Mar. 24, 2015 and entitled "SURGICAL GENERATOR FOR ULTRASONIC AND ELECTROSURGICAL DEVICES," which is hereby incorporated herein by reference in its entirety. While these generator systems possess an impressive array of capabilities, there is a continuing need for improved generator systems.

SUMMARY

Surgical generator systems and related methods are disclosed herein. An exemplary generator system can include one or more auxiliary transformer stages to boost the amount of power applied to low-impedance tissue, or to adjust the output voltage and current delivered to a surgical instrument. The auxiliary transformer stage(s) can be disposed in the generator, in the surgical instrument, and/or in an intermediate component. Exemplary generator systems can also include an accessory box disposed inline between a generator and a surgical instrument to provide expanded functionality to the system. The accessory box can have a ground plane that is isolated from the ground planes of the mains supply, the generator, and/or the surgical instrument to reduce or eliminate patient leakage current.

In some embodiments, a surgical generator system includes a generator configured to provide power for driving a surgical instrument. The system can include an output circuit that includes a first transformer having a primary coil and a secondary coil and producing a first output at the secondary coil, and an auxiliary transformer having a primary coil that receives the first output and a secondary coil at which a second output is produced. The system can also include a switching element configured to switch between outputting the first output and outputting the second output.

The second output can have one of a higher voltage than the first output and a higher current than the first output. The auxiliary transformer can be disposed in a chassis of the generator. The auxiliary transformer can be disposed in a chassis of a surgical instrument configured to be coupled to the generator. The auxiliary transformer can be disposed in an accessory box wired between the generator and a surgical instrument. The system can include a controller configured to switch the switching element based on a parameter of tissue. The parameter of the tissue can include an impedance of the tissue. The system can include a sensor in communication with the controller, the sensor being configured to sense the parameter of the tissue. The auxiliary transformer can be a first auxiliary transformer, and the system can include a second auxiliary transformer having a winding ratio that differs from the winding ratio of the first auxiliary transformer.

In some embodiments, a method of delivering energy to tissue includes engaging tissue with a surgical instrument coupled to a generator configured to provide power for driving the surgical instrument; controlling the generator to selectively include one or more auxiliary transformers in an output path between the surgical instrument and a primary transformer disposed in the generator; and delivering energy through the output path to the tissue.

Controlling the generator can include actuating a switching element to selectively include the one or more auxiliary transformers in the output path. Controlling the generator can include selectively including the one or more auxiliary transformers in the output path based on an output of a sensor configured to sense a property of the tissue. Controlling the generator can include, when an impedance of the tissue is below a threshold value, including in the output path an auxiliary transformer configured to boost the output current of the generator. Controlling the generator can include selectively including one of a plurality of auxiliary transformers in the output path, each of the plurality of auxiliary transformers having a winding ratio that differs from the winding ratios of the others of the plurality of auxiliary transformers.

In some embodiments, a surgical accessory box includes a generator port configured to couple the accessory box to a surgical generator; an instrument port configured to couple the accessory box to a surgical instrument; an electronic component coupled to at least one of the generator port and the instrument port; a chassis in which the generator port, the instrument port, and the electronic component are disposed; and an accessory box ground plane to which the electronic component is grounded that is not in electrical communication with a ground plane of a mains power supply coupled to the accessory box.

The accessory box ground plane, in some embodiments, is not in electrical communication with any ground plane external to the accessory box. In some embodiments, no electrical component in the accessory box is in electrical communication with any ground plane external to the accessory box. The accessory box ground plane, in some embodiments, is not in electrical communication with any of: the chassis, a ground plane of a generator coupled to the generator port, and a ground plane of an instrument coupled to the instrument port. The accessory box can include an AC power input having hot, neutral, and ground conductors. The ground conductor of the AC power input, in some embodiments, is coupled to the chassis and not to the electronic component. The hot and neutral conductors of the AC power input can be coupled to the electronic component. The accessory box can include an AC receptacle having hot, neutral, and ground connection points that are coupled to the hot, neutral, and ground conductors, respectively, of the AC power input. The electronic component can be or can include a power supply configured to generate a DC voltage rail. In some embodiments, all connections between the generator port and the electronic component include isolation devices. In some embodiments, all connections between the instrument port and the electronic component include isolation devices.

The present invention further provides systems and methods as claimed.

BRIEF DESCRIPTION OF THE DRAWINGS

The invention will be more fully understood from the following detailed description taken in conjunction with the accompanying drawings, in which.

DETAILED DESCRIPTION

Surgical generator systems and related methods are disclosed herein. An exemplary generator system can include one or more auxiliary transformer stages to boost the amount of power applied to low-impedance tissue, or to adjust the output voltage and current delivered to a surgical instrument. The auxiliary transformer stage(s) can be disposed in the generator, in the surgical instrument, and/or in an intermediate component. Exemplary generator systems can also include an accessory box disposed inline between a generator and a surgical instrument to provide expanded functionality to the system. The accessory box can have a ground plane that is isolated from the ground planes of the mains supply, the generator, and/or the surgical instrument to reduce or eliminate patient leakage current.

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the present invention is defined solely by the claims. The features illustrated or described in connection with one exemplary embodiment can be combined with the features of other embodiments. Such modifications and variations are intended to be included within the scope of the present invention.

Figure 1:
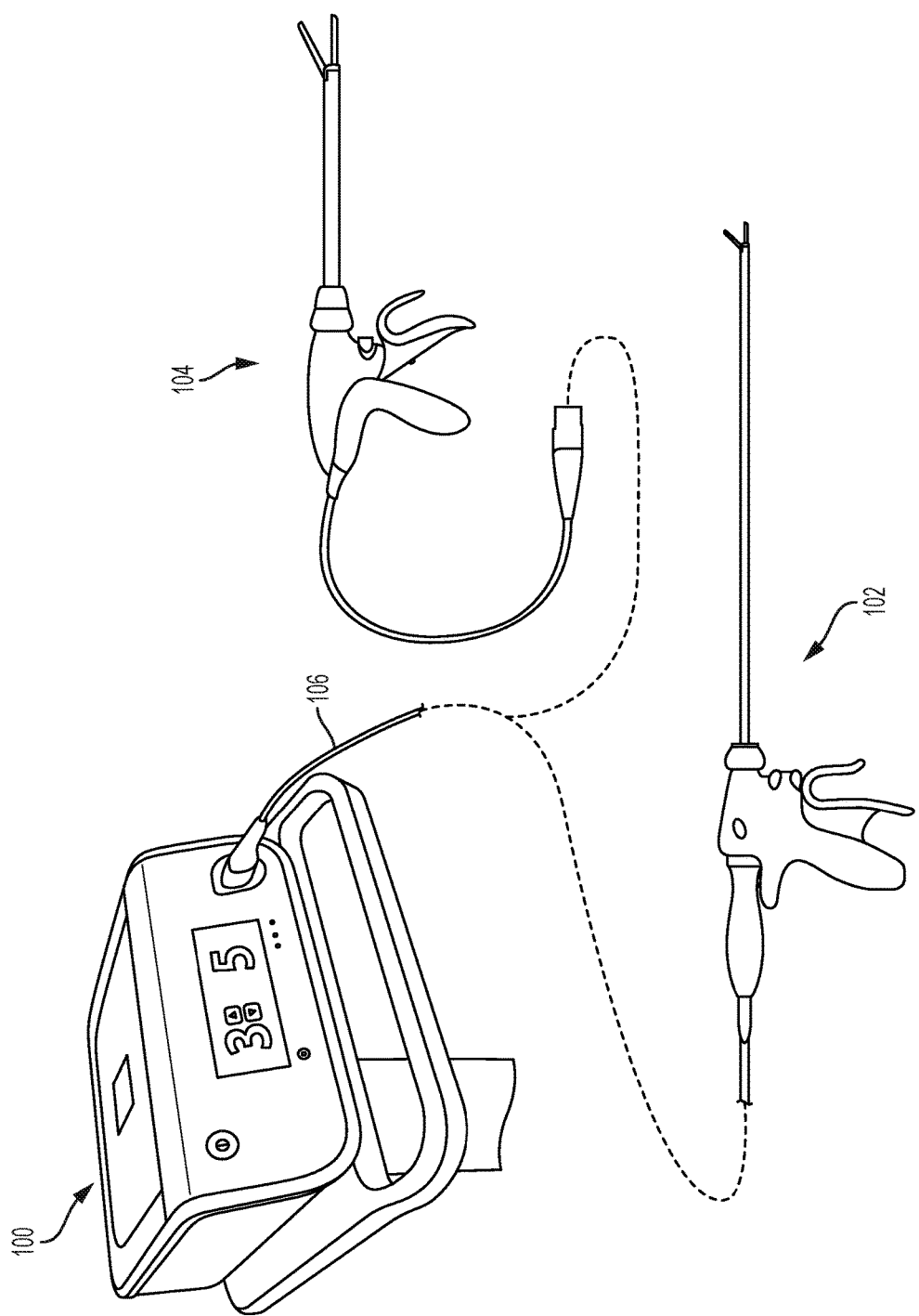
FIG. 1 is a schematic perspective view of a surgical generator system and surgical instruments that can be used with the surgical generator system.

FIG. 1 illustrates an exemplary embodiment of a surgical generator system 100 configurable for use with one or more surgical instruments. The generator system 100 can be configurable for use with surgical instruments of different types, including, for example, an ultrasonic surgical device 102 and an electrosurgical or RF surgical device 104. Although in the embodiment of FIG. 1 the generator system 100 is shown separate from the surgical devices 102, 104, in some embodiments the generator system can be formed integrally with either of the surgical devices to form a unitary surgical system.

The generator system 100 can be battery powered or can be coupled to a wall outlet or other power source. The generator system 100 can be connected to a surgical instrument via a suitable transmission medium such as a cable 106 having one or more electrical conductors disposed therein (e.g., a first conductor electrically coupled to an active electrode of the device and a second conductor electrically coupled to a return electrode of the device in the case of a bipolar electrosurgical instrument). The generator system 100 can be configured to apply a voltage differential across the first and second conductors to cause current to flow through the device and tissue being treated thereby. The generator system can include an RF source, an ultrasonic source, a direct current source, and/or any other suitable type of electrical energy source.

In some embodiments, such as for bipolar electrosurgery applications, the device 104 can include an active electrode and a return electrode, wherein the active electrode and the return electrode can be positioned against, adjacent to, and/or in electrical communication with, the tissue to be treated such that current can flow from the active electrode to the return electrode through the tissue. Thus, the generator system 100 can include a supply path (or output path) and a return path, wherein the captured tissue being treated completes, or closes, the circuit. The generator system 100 can also support monopolar electrosurgical operation and the device 104 can include a monopolar end effector in which one or more active electrodes are disposed. In such embodiments, the generator system 100 can include a return pad in intimate contact with the patient at a location remote from the operative site and/or another suitable return path. The return pad can be connected via a cable to the generator system.

Figure 2:
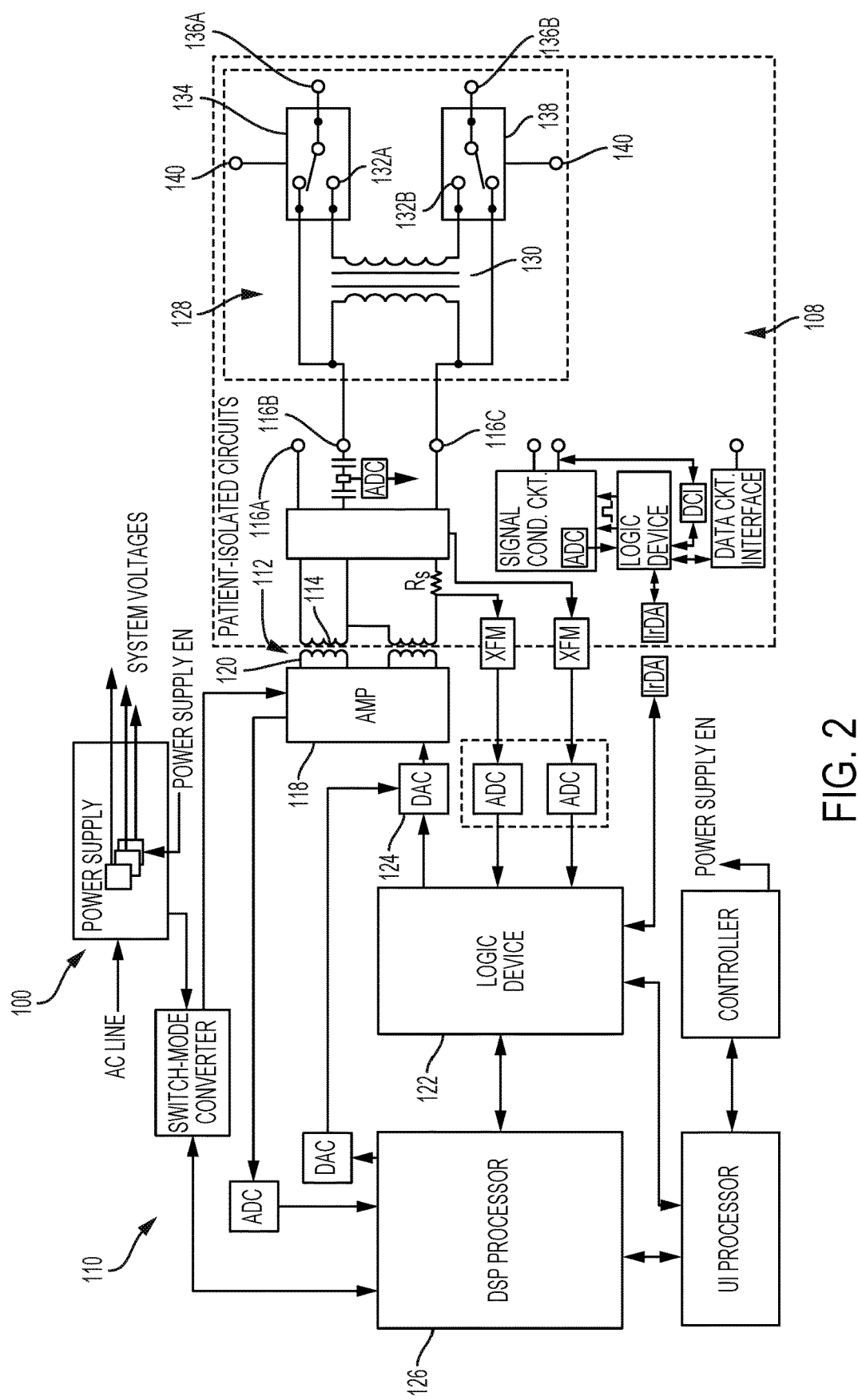
FIG. 2 is a schematic diagram of the surgical generator system of FIG. 1.

FIG. 2 is a simplified block diagram of the surgical generator system 100. As shown, the generator system 100 can include a patient isolated stage 108 in communication with a non-isolated stage 110 via a power transformer 112. A secondary winding 114 of the power transformer 112 is contained in the isolated stage 108 and can include a tapped configuration (e.g., a center-tapped or non-center tapped configuration) to define drive signal outputs 116A, 116B, 116C for outputting drive signals to different surgical devices, such as, for example, an ultrasonic surgical device 102 and an electrosurgical device 104. In particular, drive signal outputs 116A, 116C can output a drive signal (e.g., a 420V RMS drive signal) to an ultrasonic surgical device 102, and drive signal outputs 116B, 116C can output a drive signal (e.g., a 100V RMS drive signal) to an electrosurgical device 104, with output 116B corresponding to the center tap of the power transformer 112. The non-isolated stage 110 can include a power amplifier 118 having an output connected to a primary winding 120 of the power transformer 112. The non-isolated stage 110 can also include a controller or programmable logic device 122 for supplying a digital output to a digital-to-analog converter (DAC) 124, which in turn supplies a corresponding analog signal to an input of the power amplifier 118. The programmable logic device 122, by virtue of controlling the input of the power amplifier 118 via the DAC 124, can therefore control any of a number of parameters (e.g., frequency, waveform shape, waveform amplitude) of drive signals appearing at the drive signal outputs 116A, 116B, 116C. The programmable logic device 122 can implement a number of digital signal processing algorithms and/or other control algorithms to control parameters of the drive signals output by the generator system 100, on its own or in connection with a dedicated digital signal processor (DSP) 126.

In addition to the drive signal outputs 116A, 116B, 116C described above, the generator system 100 can include one or more auxiliary transformer stages configured to provide additional drive signal outputs. In the illustrated embodiment, the generator system 100 includes a single auxiliary transformer stage 128 with a second transformer 130 configured to provide a second set of drive signal outputs 132A, 132B. It will be appreciated, however, that the generator system 100 can include any number of auxiliary transformer stages. In embodiments with multiple auxiliary stages, one or more transformer properties can be varied from one stage to the next. For example, each stage can include a transformer with a different winding ratio from the other stages.

One or more switching devices can be used to selectively include each transformer stage in an output path of the generator system (e.g., to selectively couple each transformer stage to a downstream instrument). For example, as shown in FIG. 2, a first solid-state relay 134 can be configured to select between coupling the output 116B of the power transformer 112 to the downstream instrument connection 136A and coupling the output 132A of the second transformer 130 to the downstream instrument connection 136A. A similar relay 138 can be included to switch between coupling the output 116C of the power transformer 112 to the downstream instrument connection 136B and coupling the output 132B of the second transformer 130 to the downstream instrument connection 136B. In some embodiments, the relay 138 can be omitted and the outputs 116C, 132B, 136B can be coupled to a common node (e.g., ground). It will be appreciated that any of a variety of other switching devices can be used instead of or in addition to the illustrated relays.

The switching devices 134, 138 can be switched via one or more control lines 140, which can be coupled to the controller 122 or another processing device, or to a manual switch. In use, the control lines 140 can be toggled, asserted, or otherwise manipulated by the controller 122 or by a user to select which output, and thus which transformer stage, is coupled to the instrument. In some embodiments, the control and switching functions can be omitted or disabled such that power is always directed through the auxiliary transformer stage 128.

Thus, in at least one operating mode, the generator system 100 can be configured to couple a downstream surgical instrument to the drive signal outputs 116B, 116C of the power transformer 112 and, in at least one other operating mode, the generator system can be configured to couple the surgical instrument to the drive signal outputs 132A, 132B of the auxiliary transformer 130. The generator system can therefore be configured to selectively place one or more auxiliary transformer stages in the output path to the surgical instrument.

Figure 3:
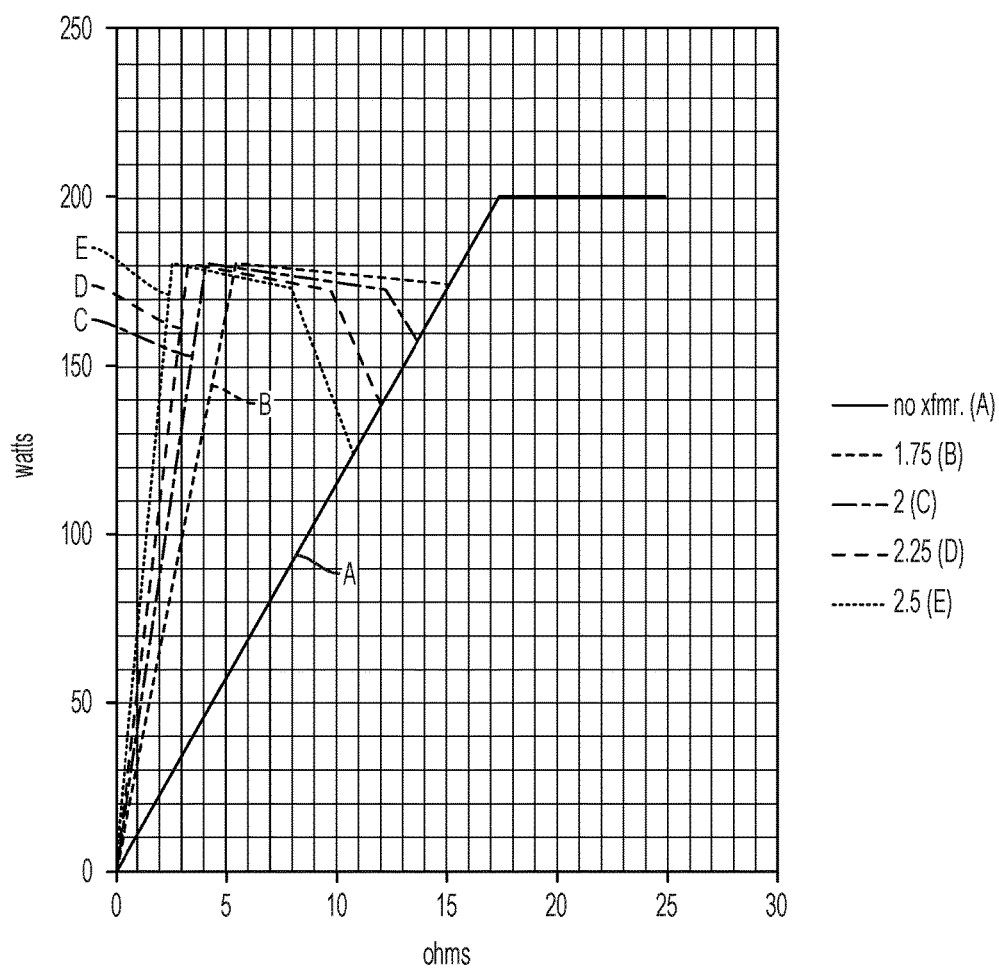
FIG. 3 is a plot of power as a function of tissue impedance for various auxiliary transformer winding ratios.

FIG. 3 is a simulated plot of power levels delivered to tissue (specified in watts) as a function of tissue impedance (specified in ohms) for an exemplary generator system 100. As shown, when the auxiliary transformer stage is not used and the instrument is driven directly from the output of the power transformer, peak power of about 200 W can be achieved with tissue having an impedance greater than about 17 ohms. For tissue having lower impedance, however, there is a drop-off in delivered power which can be significant. For example, the power is less than 50 W for tissue having an impedance between about 0 and about 4 ohms. Lower power can undesirably result in longer tissue sealing times. One factor that leads to this drop-off is that low-impedance tissue causes a large current draw from the generator, which is configured to limit its current output to protect the generator hardware. Since power is proportional to the square of the current and to the tissue impedance, the combination of limited current and low tissue impedance results in low output power.

On the other hand, when an auxiliary transformer is used to increase the output current, the delivered power increases significantly for low impedance tissue. For example, when a secondary transformer stage is employed with a 2.5:1 winding ratio (or "turns ratio"), delivered power of at least about 180 W can be achieved in tissue with an impedance of only about 2.5 ohms. Similar improvements are observed with winding ratios of 2.25:1, 2:1, and 1.75:1. As evident from FIG. 3, the power profile of the generator varies, at least in part, based on the winding ratio of the auxiliary transformer. The generator can thus be configured to switch between a plurality of auxiliary transformers, each having a different winding ratio, to select the desired power profile. In some embodiments, the generator can include a processor that receives an estimated tissue impedance value from a sensor disposed on the surgical device or elsewhere and automatically switches between auxiliary transformer stages (or switches auxiliary transformer stages on or off) based thereon. By using a transformer with the appropriate winding ratio, higher current outputs at lower tissue impedance levels can be obtained to deliver higher power. In particular, since power increases with the square of the current, higher output current can significantly increase output power. With the use of one or more auxiliary transformer stages, maximum power can be applied across a range of different impedances, which can advantageously reduce or eliminate power ramp-up times. As certain impedance levels are reached, the controller can be configured to stop using the auxiliary transformer stages and return to normal generator output.

The transformer winding ratio can also be selected to control the output current or output voltage of the system as desired by a user. In particular, an auxiliary transformer stage can be used to step down the output voltage to increase output current, or to step up the output voltage to decrease the output current. The degree to which the voltage or current is increased or decreased can be selected to tailor the generator output to a particular application. For example, as described above, higher output currents can advantageously increase the amount of power delivered to low impedance tissue. By way of further example, higher output voltages can be desirable for electroporation (reversible or irreversible). The use of auxiliary transformer stages can facilitate increasing the output voltage, as well as giving the user more-precise or more-granular voltage control.

Figure 4A:
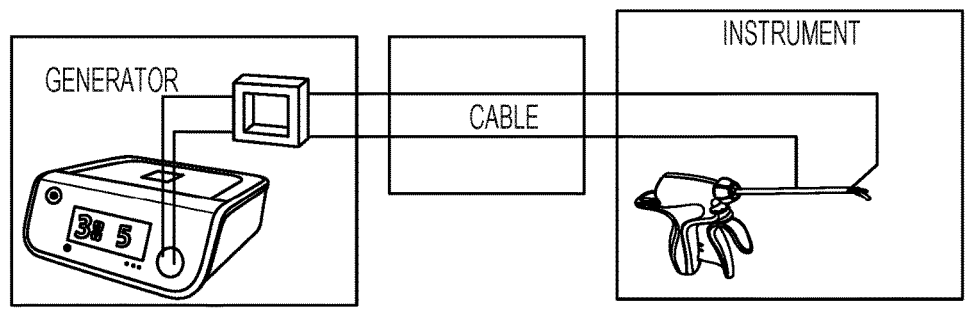
FIG. 4A is a schematic diagram of a surgical generator system in which one or more auxiliary transformer stages are housed in a generator.
Figure 4B:
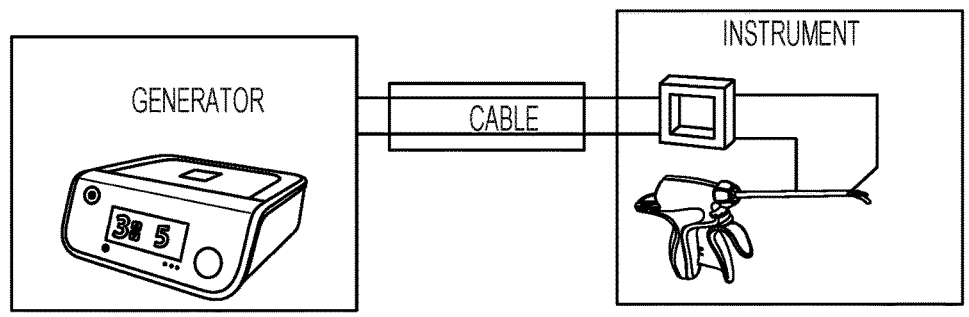
FIG. 4B is a schematic diagram of a surgical generator system in which one or more auxiliary transformer stages are housed in a surgical instrument.
Figure 4C:
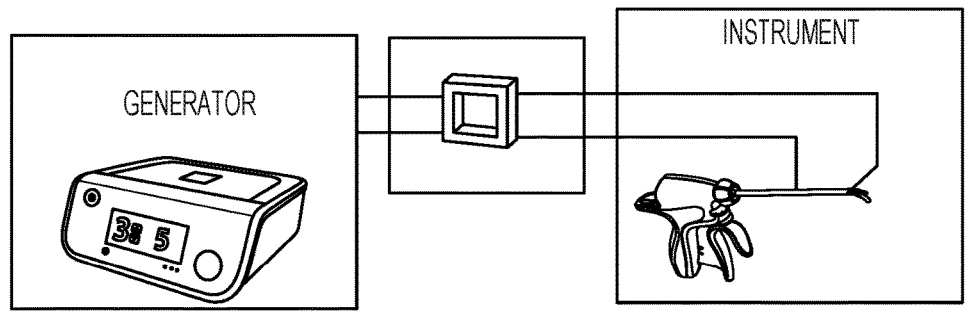
FIG. 4C is a schematic diagram of a surgical generator system in which one or more auxiliary transformer stages are disposed intermediate to the generator and the surgical instrument.

As shown schematically in FIG. 4A, one or more auxiliary transformer stages can be disposed internally to the generator chassis. Alternatively, or in addition, one or more auxiliary transformer stages can be disposed internally to the surgical instrument, as shown in FIG. 4B. Alternatively, or in addition, one or more auxiliary transformer stages can be disposed in an intermediate element disposed between the generator and the instrument, such as a cable or an accessory box, as shown in FIG. 4C and described further below.

Figure 5A:
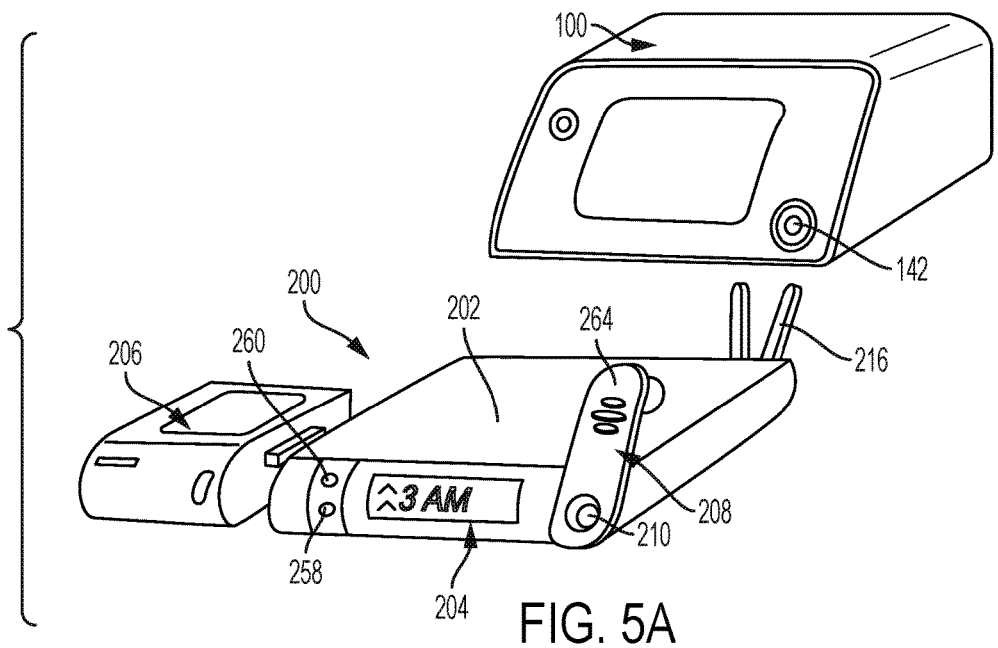
FIG. 5A is an exploded perspective view of a surgical generator system that includes an accessory box.
Figure 5B:
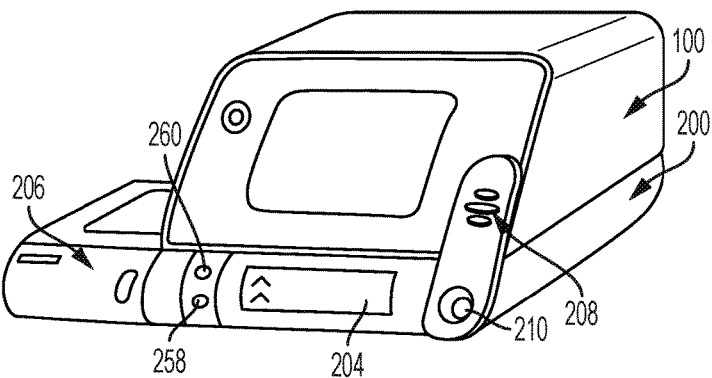
FIG. 5B is an assembled perspective view of the surgical generator system of FIG. 5A.
Figure 5C:
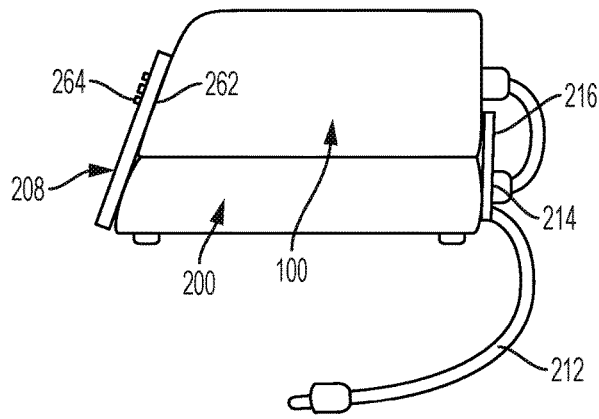
FIG. 5C is a side profile view of the surgical generator system of FIG. 5A.

FIGS. 5A-5C illustrate an exemplary embodiment of an accessory box 200 that can be used with one or more surgical instruments and a generator 100 of the type described above. The accessory box can be configured to provide additional functionality to the generator. For example, the accessory box can include one or more auxiliary transformer stages as described above. Alternatively, or in addition, the accessory box can include various other components. Use of an accessory box can advantageously add features to existing generators without requiring redesign or replacement of the generator.

The illustrated accessory box 200 generally includes a chassis 202 that houses the various electrical components of the accessory box. The chassis 202 can be sized to substantially match the footprint or other dimensions of a generator 100 with which the accessory box 200 is to be used, such that the generator can be seated on a top surface of the accessory box or vice-versa. One or more user interface elements, such as a display screen, touch screen, buttons, etc. can be mounted in the chassis to facilitate interaction with a user. For example, a touch screen 204 can be mounted in a front panel of the accessory box 200. The accessory box 200 can include an integral or detachable battery charger module 206. The accessory box 200 can also include a generator connector 208 to couple one or more electrical conductors of the accessory box to the generator 100 (e.g., via an instrument port 142 of the generator). The generator connector 208 can include a substantially flat housing as shown in or can be or can include a flexible round cable. The accessory box 200 can also include an instrument port 210 (e.g., a cable or connector) through which one or more electrical conductors of the accessory box can be coupled to one or more electrical conductors of a surgical instrument. The accessory box 200 can include a power cord 212 for connecting the accessory box to a mains power supply (e.g., an AC power supply in a hospital or other operating environment) and a power outlet 214 to which other corded electronic devices (e.g., generators) can be coupled to receive electrical power. The accessory box 200 can also include a network interface module with an internal antenna or an external antenna 216.

Figure 6:
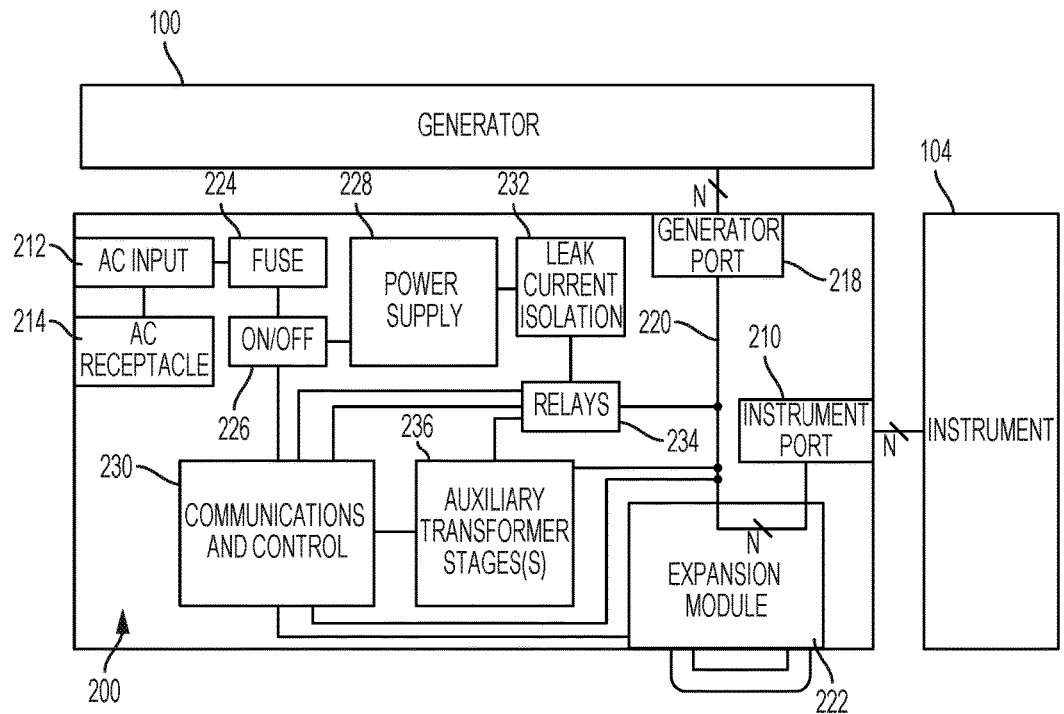
FIG. 6 is a schematic diagram of the accessory box of FIG. 5A.

FIG. 6 is a simplified block diagram of an exemplary embodiment of the accessory box 200. The accessory box 200 can include a generator port 218 through which the accessory box can be coupled to a generator 100 (e.g., via the generator connector 208 or via a cable having one or more electrical conductors therein). The generator port 218 of the accessory box 200 can be coupled to an instrument port 142 of the generator 100 which is normally used to connect the generator directly to a surgical instrument (e.g., as shown in FIG. 1). The accessory box 200 can also include one or more instrument ports 210 through which the accessory box can be coupled to one or more respective instruments (e.g., an instrument 104). The generator and instrument ports 218, 210 can include a plurality of electrical paths or lines that extend between the accessory box and the generator or instrument. In the illustrated embodiment, both ports 218, 210 include the same number N electrical conductors, though it will be appreciated that the ports 218, 210 can have a different number of conductors from one another.

The generator port 218 and in the instrument port 210 can be coupled to one another via a bus system 220. In some embodiments, the bus system can include at least as many electrical conductors as are included in the generator and instrument ports (e.g., N conductors as shown in the illustrated embodiment). The bus system 220 can allow the accessory box 200 to act as a pass-through device by which a generator 100 and a surgical instrument 104 coupled to the accessory box can work together as though they are directly coupled. As described further below, electronics within the accessory box 200 can tap into one or more lines of the bus system 220 to perform any of a variety of functions. Exemplary functions include, without limitation, communicating with the generator, communicating with the instrument, monitoring communications between the generator and the instrument, modifying communications between the generator and the instrument, adjusting a drive voltage provided to the instrument, adjusting a drive current provided to the instrument, providing a DC power supply to the instrument, reading sensor data from a sensor mounted on the instrument, receiving video or image data from a camera or image sensor mounted on the instrument, monitoring usage of the generator and/or instrument, and so forth.

In some embodiments, the accessory box 200 can include a plurality of instrument ports 210 such that the accessory box can serve as a hub for using multiple instruments with a single port 142 on the generator 100. A multiplexer or other switching logic can be included in the accessory box 200 to couple the signal and power lines of each instrument to the bus system 220 in a manner that is functionally seamless to the generator 100 and to the instrument 104. The instrument port 210 can include a grounding pad to facilitate use with monopolar electrosurgical instruments. The accessory box 200 can be configured to pass through monopolar energy provided by the generator 100, or to generate monopolar energy onboard and deliver said energy to a surgical instrument. In embodiments in which monopolar functionality is provided, the monopolar lines can be kept completely insulated from the chassis and ground of the accessory box and/or the generator.

The bus system 220 can be routed through an expansion module 222. In the illustrated embodiment, the expansion module 222 is a simple pass-through module in which electrical conductors entering the expansion module from the instrument port 210 are simply routed back out of the expansion module to the rest of the accessory box 200. In other embodiments, however, the expansion module 222 can include on-board electronics or other components configured to achieve any of the accessory box functions described herein or that may be developed in the future. The expansion module 222 can be removable and replaceable with other expansion modules to change the functionality of the accessory box 200. The expansion module 222 can be replaced in the field to quickly and easily upgrade or add functionality to the accessory box 200. In some embodiments, the expansion module 222 can be a printed circuit board or a cable that is configured to couple with one or more connectors mounted in the accessory box 200.

The accessory box 200 can be powered by AC power that enters the accessory box via a power cord or other AC input 212 and that is fed through a fuse 224 to an on/off relay 226 or other switching device. While an AC power source is shown, it will be appreciated that, in other embodiments, the accessory box 200 can be powered by an internal or external battery, or via power received from a generator or instrument through the generator port 218 or the instrument port 210, respectively. Additional exemplary ways in which the accessory box 200 can be powered are described in U.S. application Ser. No. 14/683,255, filed on Apr. 10, 2015, entitled "DEVICES AND METHODS FOR PROVIDING ADDITIONAL POWER TO SURGICAL DEVICES", now U.S. Patent Application Publication No. 2016/0296270. The on/off relay 226 can be optically isolated and can be configured to switch on and off input power to a power supply 228 based on one or more control signals received from a communications and control circuit 230. The power supply 228 can convert the AC input voltage into one or more DC voltage rails which can be isolated by a leak current isolation circuit 232. Exemplary DC voltage rails which can be generated by the power supply 228 include 48V, 12V, 5V, 3.3V, 1.8V, 1.2V, etc.

The isolated DC output(s) of the power supply 228 can be routed through one or more relays or other switching devices 234 such that supply of DC power to one or more components of the accessory box 200 or to the bus system 220 can be selectively turned on and off based on control signals generated by the communications and control circuit 230. A connection between the relays 234 and the bus system 220 can allow DC power to be supplied to the generator 100, to the instrument 104, and/or to the expansion module 222. This DC power can be used for any of a variety of purposes including, without limitation, powering a motor or sensor on a surgical instrument or powering integrated circuits disposed in the expansion module.

One or more auxiliary transformer stages 236 of the type described above can be included in the accessory box 200 to modify the output of the generator 100 before it is fed to the surgical instrument 104. The auxiliary transformer stages 236 can be selectively connected and disconnected based on control signals received from the communications and control circuit 230. For example, the communications and control circuit 230 can be configured to change the voltage level on a control line connected to a relay or other switching device within the auxiliary transformer stage 236 to switch the relay. Switching the relay can be effective to disconnect a transformer of the auxiliary transformer stage 236 from the bus system 220 and thus from the surgical instrument 104. The accessory box 200 can also be configured to modify the output of the generator 100 in other ways. For example, the accessory box 200 can include circuitry that modifies or conditions the output waveform of the generator 100 to change from a first wave shape (e.g., sinusoidal) to a second, different wave shape (e.g., trapezoidal or a DC-like pulse).

The communications and control circuit 230 can include any of a variety of components for controlling the various features of the accessory box 200 and for communicating with the generator 100 and/or the surgical instrument 104.

Figure 7:
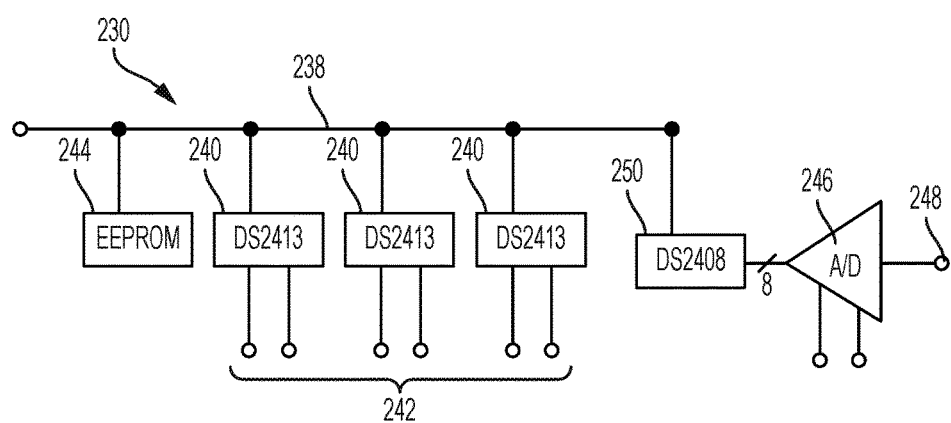
FIG. 7 is a schematic diagram of the communications and control circuit of FIG. 7.

FIG. 7 illustrates an exemplary embodiment of a communications and control circuit 230. The circuit 230 is coupled to the bus system 220 and, ultimately, to the generator 100, via a communications interface 238 (e.g., a 1-Wire® communications interface). The communications interface can allow for communication with, and control of, the accessory box 200 by a remote device such as the generator 100. The circuit 230 also includes one or more programmable I/O chips 240 that receive commands via the communications interface 238 and control one or more I/O lines 242 based on those commands. An exemplary programmable I/O chip 240 is the DS2413 dual-channel programmable I/O 1-Wire chip available from Maxim Integrated Products, Inc. The I/O lines 242 can include leakage current isolation hardware (e.g., optical isolators) for patient protection. The I/O lines 242 can be used to enable or disable various features of the accessory box 200, such as to turn on or off the power supply 228, to divert RF output through one or more auxiliary transformer stages 236, to turn on or off DC outputs (e.g., by controlling a transistor switch), or to turn on/off network connectivity.

The circuit 230 can also include a storage device 244 (e.g., an EEPROM) that stores information which can be read and/or written via the communications interface 238. In some embodiments, the storage device 244 stores a unique identifier or other information that can be read by the generator 100 over the communications interface 238 to identify the accessory box 200 to the generator and to inform the generator of the capabilities or other attributes of the accessory box. The circuit 230 can also include an A/D converter 246 configured to convert analog data (e.g., the output of a sensor disposed on the surgical instrument 104) into a digital signal which can be communicated to the generator 100 over the communications interface 238. In the illustrated embodiment, an 8-bit A/D converter 246 converts an analog input 248 into 8 digital outputs which are communicated over the communications interface 238 by an 8-channel programmable I/O chip 250 (e.g., a DS2408 8-channel programmable I/O 1-wire chip available from Maxim Integrated Products, Inc.).

While a 1-wire interface is described in the above exemplary embodiment, it will be appreciated that any of a variety of communications interfaces 238 can be used instead or in addition, including I2C, USB, SPI, CAN, RS-232, RS-485, and the like. Each of the various types of communication interfaces can provide unique advantages. For example, use of an I2C communication interface can advantageously allow communication with a gamma-sterilizable I2C-based EEPROM disposed in a surgical instrument. In some embodiments, multiple communication interfaces can be used. For example, the accessory box 200 can be configured to convert a communications interface used by the generator 100 to one which is used by a surgical instrument 104. In other words, the accessory box 200 can communicate with the generator using a first communication interface and communicate with the surgical instrument 104 using a second, different communication interface. The accessory box 200 can thus allow use of surgical instruments 104 that employ a communications scheme not supported by the generator 100 alone.

Figure 8:
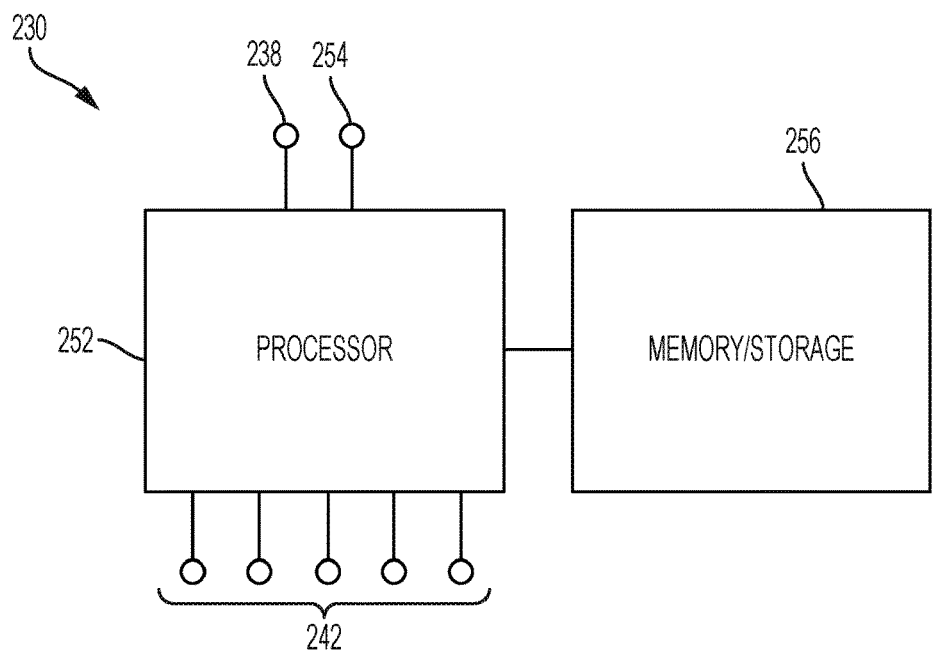
FIG. 8 is another schematic diagram of the communications and control circuit of FIG. 7.

As an alternative to the above circuit 230, or in addition thereto, the accessory box can include an onboard controller. FIG. 8 illustrates an exemplary embodiment of a communications and control circuit 230 that includes a controller 252 (e.g., a digital data processor, a FPGA, an ASIC, etc.). The controller 252 can be coupled to the bus system 220 and, ultimately, to the generator, via any of the communications interfaces 238 described above or otherwise known to those skilled in the art. The controller can also include one or more digital or analog I/O lines 242 (e.g., GPIO pins) for controlling components of the accessory box 200, receiving sensor data, etc. The controller can be powered by one or more DC power rails 254 generated by the power supply 228. The circuit 230 can also include a memory or storage device 256 for storing code to be executed by the controller 252 or for storing data that is processed by the controller. Software (e.g., firmware, device drivers, operating systems, application programs, etc.) for execution by the controller 252 can be downloaded and stored in the memory or storage device 256. For example, the controller 252 can be configured to receive software upgrades via a USB connection to a flash memory drive or via a Wi-Fi, cellular data, or Bluetooth network connection, store the software upgrades in the storage device 256, perform various authentication, verification, and installation steps, and begin executing the upgraded software.

In some embodiments, the controller 252 can be or can include a PLC or a microcontroller board such as those available from Arduino SA. The controller 252 can receive voltage inputs from sensors, user interface elements such as buttons or touch screens, and so forth. The controller 252 can also send voltage outputs to control various devices such as motors, display screens, speakers, lights, pumps, the generator RF or ultrasound algorithm, a network interface, etc.

One or more inputs or outputs to the communications and control circuit 230 can be routed to the expansion module 222 or to an exterior panel of the accessory box 200 to facilitate future upgrades. In some embodiments, such upgrades can be performed externally without accessing the interior of the accessory box chassis, which can advantageously facilitate simple field upgrades.

The accessory box 200 can include an image or video input port 258 (shown in FIG. 5A) through which a camera or image sensor can be coupled to the accessory box. The camera or image sensor can be mounted on a surgical scope or on the distal end of an energy delivery instrument plugged into the accessory box. Positioning a camera at the distal end of an ultrasonic or RF surgical instrument can advantageously provide improved visibility when the instrument is used in an area which is not easily accessible using a surgical scope (e.g., the lower portions of a male abdomen). The image or video port 258 can be a standalone port (e.g., on a front panel of the accessory box as shown in FIG. 5A), or can be integrated with the instrument port 210 of the accessory box. The accessory box can be configured to pass a video or image feed that it receives through an image or video output port 260 to an external device such as a monitor for viewing by a surgeon. The accessory box 200 can also be configured to perform various processing or analysis functions on the received video or image feed.

The accessory box 200 can include a battery charger 206 that leverages the DC power supply 228 in the accessory box to charge various devices that may be used in the operating environment. The battery charger 206 can be a wireless pad-type charger, or can include one or more wired connectors for attaching to a battery or a battery-powered device.

While not shown in the above embodiments, the communications and control circuit 230 can also include a network interface module configured to communicatively couple the accessory box 200 to one or more networks. For example, the circuit 230 can include a cellular data controller with associated antenna, an Ethernet or Wi-Fi controller with associated port or antenna, a Bluetooth controller with associated antenna, etc. Providing network access to the generator system 100 can facilitate a number of beneficial features. For example, proper device operation can be monitored remotely over the network (e.g., by a device manufacturer), or the network can be used to download software upgrades to the generator, the accessory box, and/or the instrument. The network connection can also allow usage of the generator and/or the instrument to be logged for billing, scheduling, proactive ordering or replacement, maintenance, Electronic Health Records (EHR), and/or sterilization purposes. A network connection can also facilitate remote troubleshooting of the system by technical support personnel. Usage data can be transmitted over the network connection to a device manufacturer for analysis and development of improved product features, energy delivery algorithms, etc.

The network connection can also be used to obtain a current time and/or date from a trusted network time server. This can allow usage timestamps to be logged to detect when an instrument or other component of the system is being used. Unauthorized sterilization or reprocessing of an instrument can be flagged when an instrument is used on different dates without an intervening approved reprocessing event or in other situations that suggest unauthorized activity. The system can also be configured to automatically disable use of the instrument when such unauthorized activity is detected (e.g., by disconnecting a drive circuit from the surgical instrument). In addition to receiving a network time, or as an alternative, the accessory box can include an onboard real-time clock and associated battery to provide accurate timestamps of system usage and detection of unauthorized activity.

In some embodiments, the network interface module can include a system for interfacing a 1-wire network (e.g., a 1-wire network that extends through the accessory box to couple a generator to a surgical instrument) with an Ethernet network. Exemplary interface systems of this type include the OW-SERVER-ENET-2 Ethernet available from Embedded Data Systems, LLC.

In some embodiments, the network interface module can include a system for interfacing a 1-wire network (e.g., a 1-wire network that extends through the accessory box to couple a generator to a surgical instrument) with a Wi-Fi network. Exemplary interface systems of this type include the OW-SERVER-ENET-2 Wi-Fi available from Embedded Data Systems, LLC.

Network connectivity can also be added to an existing generator independently of the accessory box, e.g., as part of a field upgrade. In some embodiments, the network interface module can include a USB-to-Ethernet adapter configured to plug into a USB port of a generator to provide network connectivity. In some embodiments, the network interface module can include a USB-to-Wi-Fi adapter configured to plug into a USB port of a generator to provide network connectivity. In some embodiments, the network interface module can include a USB-to-Ethernet or USB-to-Wi-Fi adapter that is integrated with a storage device such as a USB flash drive and a USB hub to allow the network adapter and storage device to be plugged into a single USB port of the generator.

As noted above, the accessory box can be coupled to the generator via a cable having one or more electrical conductors therein that plugs into an instrument port of the generator. In some embodiments, a shown in FIGS. 5A-5C, the cable can be or can include a flat housing 208 that is rigid or semi-rigid. The housing 208 can include a first, rearward-facing, substantially-planar surface 262 having a generator connector formed therein or extending therefrom for coupling the housing 208 to the generator's instrument port 142 and an accessory box connector formed therein or extending therefrom for coupling the housing to the accessory box's generator port 218. The housing 208 can also include a second, forward-facing, substantially-planar surface 264 facing opposite to the first surface 262 and having one or more connectors 210 formed therein or extending therefrom for coupling the housing to one or more respective instruments. The housing 208 can cover the existing instrument port 142 on the generator 100 such that only the ports in the housing and/or the accessory box 200 are available for attaching an instrument. The illustrated housing 208 can advantageously eliminate operator confusion by making the port or ports of the accessory box 200 the only apparent available port and provide an aesthetically pleasing solution for coupling the accessory box to the generator 100 (e.g., avoiding the use of unnecessarily long cables to couple the accessory box to the generator).

As noted above, the pin configuration of the instrument port 210 of the accessory box 200 can match that of the generator's instrument port 142, such that signals can be passed seamlessly from the instrument, through the accessory box, and into the generator and vice versa. The accessory box can also be configured to modify one or more signals passing therethrough on the way to the generator or the instrument. For example, the accessory box can augment or replace an RF signal produced by the generator for powering the instrument, for example by adjusting a current or voltage of the signal.

Reducing or eliminating patient leakage current can be an important safety consideration in the design of surgical generator systems of the type disclosed herein. In some jurisdictions, standards for safety and effectiveness such as the IEC 60601-1 standard for electronic medical equipment published by the International Electrotechnical Commission dictate the maximum permissible leakage current of a device. Even moderate levels of patient leakage current can be dangerous to the patient or operating room personnel. One way in which patient leakage current can occur is when current flows from an applied part (e.g., a surgical instrument) through the patient to earth. The path from the patient to earth need not necessarily be back through the applied part. Another way in which patient leakage current can occur is when current flows from some other source of voltage potential through the patient to earth via the applied part.

In some embodiments, the accessory box 200 can include features for minimizing or eliminating patient leakage current. For example, if the ground plane of the accessory box 200 is kept separate or floating, there is no path to ground through which patient leakage current can flow through the accessory box. This can advantageously provide for a safer piece of equipment and require less-rigorous design and testing of leakage currents.

Figure 9:
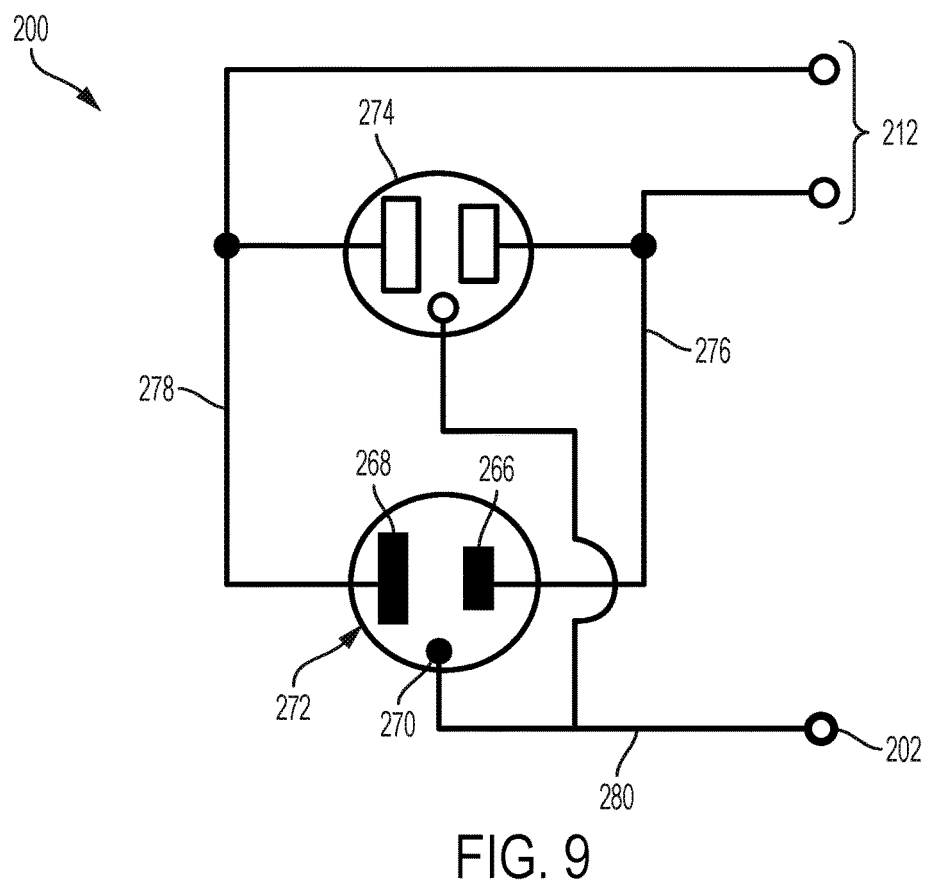
FIG. 9 is a schematic diagram of a ground plane isolation circuit of the accessory box of FIG. 5A.

FIG. 9 illustrates an exemplary embodiment of an accessory box 200 with a split system power architecture to reduce or eliminate patient leakage current through the accessory box. As shown, the accessory box is coupled to the hot, neutral, and ground leads 266, 268, 270 of a mains power supply via a standard 3-wire plug 272. The hot, neutral, and ground leads 266, 268, 270 are electrically coupled via respective hot, neutral, and ground electrical conductors 276, 278, 280 to an AC receptacle 274, where they can in turn be coupled to respective hot, neutral, and ground leads of a generator or other corded electronic device. In some embodiments, power conditioning circuitry can be included in the accessory box 200 between the plug 272 and the AC receptacle 274 to provide conditioned power to a generator or other load plugged into the AC receptacle 274. Exemplary power conditioning circuitry can include voltage regulator circuits, noise suppression circuits, and/or surge protection circuits. The ground conductor 280 is also electrically coupled to the chassis 202 of the accessory box 200 to allow safe contact with the exterior of the accessory box. The hot and neutral conductors 276, 278 are electrically coupled to the electronics within the accessory box to provide power thereto (e.g., where the AC input 212 meets the fuse 224 in FIG. 6).

While the ground conductor 280 is electrically coupled to the accessory box chassis 202, in some embodiments it is not electrically coupled to any of the electronic components of the accessory box 200. Rather, all of the electronic components of the accessory box 200 can be isolated from the chassis 202, for example using insulating materials or physical separation. Thus, the electronic components do not interact with the chassis 202 or the ground conductor 280 and, by extension, the ground of the mains supply, and therefore no leakage path exists between the accessory box electronics and earth.

In some embodiments, possible leakage paths can be further eliminated by ensuring that all of the connection paths between the generator 100 and the accessory box 200 do not connect to an additional ground or electrically connect to the output of the power supply 228. Rather, the connection paths can include various isolation circuits to prevent such connections, including opto-isolators, isolation transformers, and the like. The accessory box 200 can thus have a ground plane that is entirely separate from the mains supply ground and/or the ground plane of the generator. Also in some embodiments, possible leakage paths can be further eliminated by ensuring that all of the connection paths between the surgical instrument 104 and the accessory box 200 do not connect to an additional ground or electrically connect to the output of the power supply 228. The accessory box 200 can thus have a ground plane that is entirely separate from the ground plane of the surgical instrument.

As the above-described systems are merely exemplary embodiments, it will be appreciated that the features of any particular system can be incorporated into any other system without departing from the scope of the present disclosure. Various embodiments of surgical instruments that utilize therapeutic and/or sub-therapeutic electrical or ultrasonic energy to treat tissue are disclosed herein. These embodiments can be configured for use in a manual or hand-operated manner, or can be utilized in robotic applications.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices described herein can be processed before surgery. First, a new or used device is obtained and if necessary cleaned. The device can then be sterilized. In one sterilization technique, the device is placed in a closed and sealed container, such as a plastic or TYVEK bag. The container and device are then placed in a field of radiation that can penetrate the container, such as gamma radiation, x-rays, or high-energy electrons. The radiation kills bacteria on the device and in the container. The sterilized device can then be stored in the sterile container. The sealed container keeps the device sterile until it is opened in the medical facility.

The devices described herein can be sterilized. This can be done by any number of ways known to those skilled in the art including beta or gamma radiation, ethylene oxide, steam, and a liquid bath (e.g., cold soak).

Although the invention has been described by reference to specific embodiments, it should be understood that numerous changes can be made within the spirit and scope of the inventive concepts described. Accordingly, it is intended that the invention not be limited to the described embodiments, but that it have the full scope defined by the language of the following claims.

The invention claimed is:

1. A surgical generator system, comprising:
    a generator configured to provide power for driving a surgical instrument;
    an output circuit that includes:
        a first transformer comprising a primary coil and a secondary coil and producing a first output at the secondary coil; and
        an auxiliary transformer comprising an auxiliary primary coil that receives the first output and an auxiliary secondary coil at which a second output is produced;
    a switching element configured to cause the output circuit to switch between outputting the first output and outputting the second output;
    a sensor configured to sense a parameter of a tissue; and
    a controller coupled to the sensor and the switching element, the controller configured to control the switching element according to the parameter of the tissue sensed via the sensor.

2. The generator system of claim 1, wherein the second output has one of a higher voltage than the first output and a higher current than the first output.

3. The generator system of claim 1, wherein the auxiliary transformer is disposed in a chassis of the generator.

4. The generator system of claim 1, wherein the auxiliary transformer is disposed in a chassis of the surgical instrument configured to be coupled to the generator.

5. The generator system of claim 1, wherein the auxiliary transformer is disposed in an accessory box wired between the generator and the surgical instrument.

6. The generator system of claim 1, wherein the parameter of the tissue comprises an impedance of the tissue.

7. The generator system of claim 1, wherein the auxiliary transformer is a first auxiliary transformer and wherein the generator system further comprises a second auxiliary transformer having a winding ratio that differs from the winding ratio of the first auxiliary transformer.

8. A method of delivering energy to tissue, comprising:
    engaging tissue with a surgical instrument coupled to a generator configured to provide power for driving the surgical instrument;
    sensing a parameter of the tissue;
    selectively switching in an output path from the surgical instrument to a primary transformer disposed in the generator between a first output of the primary transformer and a second output of one or more auxiliary transformers according to the parameter of the tissue; and
    delivering energy through the output path to the tissue.

9. The method of claim 8, wherein selectively switching in the output path comprises actuating a switching element to selectively include the one or more auxiliary transformers in the output path.

10. The method of claim 8, wherein selectively switching in the output path comprises selectively including the one or more auxiliary transformers in the output path based on an output of a sensor configured to sense a property of the tissue.

11. The method of claim 8, wherein selectively switching in the output path comprises including in the output path an auxiliary transformer configured to boost an output current of the generator when an impedance of the tissue is below a threshold value.

12. The method of claim 8, wherein selectively switching in the output path comprises selectively including one of a plurality of auxiliary transformers in the output path, each of the plurality of auxiliary transformers having a winding ratio that differs from the winding ratios of the others of the plurality of auxiliary transformers.

* * * * *